US010391084B2

(12) United States Patent
Whitsett et al.

(10) Patent No.: US 10,391,084 B2
(45) Date of Patent: Aug. 27, 2019

(54) METHODS AND COMPOSITIONS TO TREAT CANCER

(71) Applicant: CHILDREN'S HOSPITAL MEDICAL CENTER, Cincinnati, OH (US)

(72) Inventors: Jeffrey Whitsett, Cincinnati, OH (US); Yutaka Maeda, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 15/901,091

(22) Filed: Feb. 21, 2018

(65) Prior Publication Data
US 2018/0177768 A1 Jun. 28, 2018

Related U.S. Application Data

(62) Division of application No. 14/897,539, filed as application No. PCT/US2014/043029 on Jun. 18, 2014, now abandoned.

(60) Provisional application No. 61/837,436, filed on Jun. 20, 2013.

(51) Int. Cl.
A61K 31/429 (2006.01)
A61P 35/00 (2006.01)

(52) U.S. Cl.
CPC ................. A61K 31/429 (2013.01)

(58) Field of Classification Search
CPC ..................... A61K 31/429; C07D 513/04
USPC .................. 514/368, 367, 366, 154; 548/154
See application file for complete search history.

(56) References Cited

U.S. PATENT DOCUMENTS

| 9,168,257 | B2 | 10/2015 | Starczynowski et al. |
| 9,664,682 | B2 | 5/2017 | Baron |
| 9,855,273 | B2 | 1/2018 | Starczynowski et al. |
| 2010/0278921 | A1 | 11/2010 | Fischer et al. |
| 2013/0085157 | A1 | 4/2013 | Smith et al. |
| 2016/0113909 | A1 | 4/2016 | Whitsett et al. |
| 2018/0177768 | A1 | 6/2018 | Whitsett et al. |

FOREIGN PATENT DOCUMENTS

WO   WO 2010/094009 A2   8/2010

OTHER PUBLICATIONS

Webb et al. Biochemical Pharmacology 2014, 87, 121-130.*
National Center for Biotechnology Information. PubChem Substance Database (CID=15991416, https://pubchem.ncbi.nlm.nih.gov/compound/15991416 (accessed Nov. 21, 2018).*
Easton et al. Oncogene 2006, 25, 6436-6446.*
Huang et al. Expert Opin Ther Pat 2011, 21 (9), 1285-1292.*
Ayoola A, et al., Primary and Acquired Resistance to Epidermal Growth Factor Receptor Tyrosine Kinase Inhibitors in Non-small Cell Lung Cancer: An Update, Cancer Invest. 2012;30:433-46.
Choi YL, et al., EML-4ALK Mutations in Lung Cancer that Confer Resistance to ALK Inhibitors, N. Engl. J. Med. 2010;363:1734-9.
Ezquerra L, et al., Midkine, a newly discovered regulator of the renin-angiotensin pathway in mouse aorta: Significance of the pleiotrophin/midkine developmental gene family in angiotensin II signaling, Biochem. Biophys. Res. Commun. 2005;333:636-43.
Ferlay J, et al., Estimates of worldwide burden of cancer in 2008 GLOBOCAN 2008, Int. J. Cancer 2010;127:2893-917.
Hao, et al., Inhibition of the Growth Factor MDK/Midkine by a Novel Small Molecule Compound to Treat Non-Small Cell Lung Cancer. PLOS One 8(8):1-8 (2013).
Heist RS, et al., Genetic Changes in Squamous Cell Lung Cancer, A Review, J. Thorac. Oncol. 2012;7:924-33.
Horiba M, et al., Neointima formation in a restenosis model is suppressed in midkine-deficient mice, J. Clin. Invest. 2000;105:489-95.
Ikematsu S, et al., Serum midkine levels are increased in patients with various types of carcinomas, Br. J. Cancer 2000;83:701-6.
Jemal A, et al., Global Cancer Statistics, CA-Cancer J. Clin. 2011;61:69-90.
Jin Z, et al., Midkine Enhances Soft-Tissue Sarcoma Growth: A Possible Novel Therapeutic Target, Clin. Cancer Res. 2008;14:5033-42.
Kobayashi S, et al., EGFR Mutation and Resistance of Non-Cmall-Cell Lunch Cancer to Gefitinib, N. Engl. J. Med. 2005;352:786-92.
Kwak EL, et al., Anaplastic Lymphoma Kinase Inhibition in Non-Small-Cell Lunch Cancer, N. Engl. J. Med. 2010;363:1693-703.
Maeda Y, et al., PARP-2 Interacts with TTF-1 and Regulates Expression of Surfactant Protein-B, J Biol Chem.;281:9600-6.
Maruyama K, et al., Midkine, a Heparin-Binding Growth Factor, Is Fundamentally Involved in the Pathogenesis of Rheumatoid Arthritis, Arthritis Rheum. 2004;50:1420-9.
Matsui T, et al., Midkine inhibitors: application of a simple assay procedure to screening of inhibitory compounds, Int. Arch. Med. 2010;3:12.
Miyauchi M, et al., Expression of Herpes Simplex Virus-Thymidine Kinase Gene Controlled by a Promoter Region of the Midkine Gene Confers Selective Cytotoxicity to Ganciclovir in Human Carcinoma Cells, Int. J. Cancer. 2001;91:723-7.
Muramatsu T., Midkine and Pleiotrophn: Two Related Proteins Involved in Development, Survival, Inflammation and Tumorigenesis, J. Biochem. 2002;132:359-71.
Ogawa N, et al., Novel Combination Therapy for Human Colon Cancer with Adenovirus-Mediated Wild-Type p53 Gene Transfer and DNA-Damaging Chemotherapeutic Agent, Int. J. Cancer. 1997;73:367-70.
Owada K, et al., Midkine Inhibits Caspase-Dependent Apoptosis via the Activation of Mitogen-Activated Protein Kinase and Phosphatidylinositol 3-Kinase in Cultured Neurons, J. Neurochem. 1999;73:2084-92.
Perez-Moreno P, et al., Squamous Cell Carcinoma of the Lung: Molecular Subtypes and Therapeutic Opportunities, Clin. Cancer Res. 2012;18:2443-51.
PUBCHEM, Compound Summary for CID 16451693, create date: Jul. 30, 2007. [retrieved on Nov. 18, 2014]. Retrieved from the internet. <URL: https://pubchem.ncbi.nlm.nih.gov/compound/16451693,?from=summary>.

(Continued)

Primary Examiner — Irina Neagu
(74) Attorney, Agent, or Firm — Frost Brown Todd LLC

(57) ABSTRACT

Embodiments provided herein relate to methods and compositions for treating cancer. Some embodiments include treating lung cancers and renal cancers.

9 Claims, 11 Drawing Sheets

(56) References Cited

OTHER PUBLICATIONS

PUBCHEM, Compound Summary for CID 4636717. Create date: Sep. 16, 2005 [retrieved on Sep. 8, 2014]. Retrieved from the Internet. <URL: http://pubchem.ncbi.nlm.nih.gov/summary/summary.cgi?cid+4636717&from=compound>.
Schiller JH, et al. Comparison of Four Chemotherapy Regimens for Advanced Non-Small-Cell Lung Cancer, N. Engl. J. Med. 2002;346:92-8.
Shimada H, et al., Preoperative serum midkine concentration is a prognostic marker for esophageal squamous cell carcinoma, Cancer Science. 2003;94:628-32.
Takei Y, et al., 5'-, 3'-Inverted-thymidine-modified antisense oligodeoxynucleotide targeting midkine,: its design and application for cancer therapy, J. Biol. Chem. 2002;277:23800-6.
Takeuchi K, et al., REI, ROS1 and ALK fusions in lung cancer, Nat. Med. 2012;18:378-81.
Tomizawa M, et al., A promoter region of the midkine gene that is frequently expressed in human hepatocellular carcinoma can activate a suicide gene as effectively as the a-fetoprotein promoter, Br. J. Cancer 2003;89:1086-90.
Tsutsui J, et al., A New Family of Heparin-binding Growth/Differentiation Factors: Increased Midkine Expression in Wilms' Tumor and Other Human Carcinomas, Cancer Res. 1993;53:1281-5.
Zakowski MF, et al., EGFR Mutations in Small-Cell Lung Cancers in Patients Who Have Never Smoked, N. Engl. J. Med. 2006;355:213-5.
Magnuson B., et al., Regulation and function of ribosomal protein S6 kinase (S6K) within Mtor signaling networks, (2012) Biochem J. 441:1-21.
Salmond, R.S. et al., MAPK, phosphatidylinositol 3-kinase, and mammalian target of rapamycin pathways converge at the level of ribosomal protein S6 phosporylation to control metabolic signaling in SD8T cells, (2009) J Immunol 183:7388-7397.
Morales, et al., Surfactants: their critical role in enhancing drug delivery to the lungs, Ther. Deliv., 2011, 2(5):623-641.
STN Registry Compound CAS No. 618391-40-5, Entered STN: Nov. 19, 2003, Supplier AKos Consulting and Solutions GmbH, STN search of Nov. 16, 2016, 1 page.
STN Registry Compound CAS No. 618391-42-7, Entered STN: Nov. 19, 2003, Supplier AKos Consulting and Solutions GmbH, STN search of Nov. 16, 2016, 1 page.
STN Registry Compound CAS No. 618391-44-9, Entered STN: Nov. 19, 2003, Supplier AKos Consulting and Solutions GmbH, STN search of Nov. 16, 2016, 2 pgs.
STN Registry Compound CAS No. 618391-46-1, Entered STN: Nov. 19, 2003, Supplier AKos Consulting and Solutions GmbH, STN search of Nov. 16, 2016, 1 page.
STN Registry Compound CAS No. 618391-48-3, Entered STN: Nov. 19, 2003, Supplier AKos Consulting and Solutions GmbH, STN search of Nov. 16, 2016, 1 page.
STN Registry Compound CAS No. 881970-33-8, Entered STN: Apr. 26, 2006, Supplier Otava, STN search of Nov. 16, 2016, 1 page.
STN Registry Compound CAS No. 881970-49-6, Entered STN: Apr. 26, 2006, Supplier Otava, STN search of Nov. 16, 2016, 1 page.
STN Registry Compound CAS No. 881970-80-5, Entered STN: Apr. 26, 2006, Supplier Otava, STN search of Nov. 16, 2016, 2 pgs.
STN Registry Compound CAS No. 881970-87-2, Entered STN: Apr. 26, 2006, Supplier Otava, STN search of Nov. 16, 2016, 1 page.
STN Registry Compound CAS No. 881970-95-2, Entered STN: Apr. 26, 2006, Supplier Otava, STN search of Nov. 16, 2016, 1 page.
STN Registry Compound CAS No. 881971-03-5, Entered STN: Apr. 26, 2006, Supplier Otava, STN search of Nov. 16, 2016, 1 page.
Gandhi, et al., "Phase I Study of Navitoclax (ABT-263), a Novel Bcl-2 Family Inhibitor, in Patients With Small-Cell Lung Cancer and Other Solid Tumors", J Clin Oncol., Mar. 2011, 29(7):909-916.
Gennaro, AR., Ed., Remington's Pharmaceutical Sciences, 18th Ed., 1990, Mack Publishing Company, Easton, PA, TOC in 5 pgs.
Gennaro, AR., Ed., Remington: The Science and Practice of Pharmacy, 19th Ed., TOC in 15 pgs.
PUBCHEM, Compound Summary for CID 15991417. Create date: Mar. 27, 2007, Retrieved from the Internet. <URL: https://pubchem.ncbi.nlm.nik.gov/compound/15991417#section=Depositor-Supplied-Patent-Identifiers> XP00275729, 15 pgs.
PUBCHEM, Compound Summary for CID 4636718. Create date: Sep. 16, 2005, Retrieved from the Internet. <URL: https://pubchem.ncbi.nlm.nik.gov/compound/4636718#section=Top>, XP002765728, 15 pgs.
International Search Report and Written Opinion dated Dec. 10, 2014 for Application No. PCT/US2014/043029, 18 pgs.
International Search Report and Written Opinion dated Oct. 20, 2017 for Application No. PCT/US2017/044335, 12 pgs.
European Search Report, Supplementary, and Written Opinion dated Jan. 27, 2017 for Application No. EP 14814014.8, 8 pgs.
U.S. Office Action, Non-Final, dated Dec. 2, 2016 for U.S. Appl. No. 14/897,539, 17pgs.
U.S. Appl. No. 61/837,436, filed Jun. 20, 2013.
U.S. Appl. No. 62/367,832, filed Jul. 28, 2016.

* cited by examiner

| Example | Structure | Western blot | Protein detected |
|---|---|---|---|
| 7 | (3-CF3-benzyl)-thiazolo-imidazole-coumarin structure | | Midkine (H441) |
| | | | Actin (H441) |
| 8 | (4-methylbenzyl)-thiazolo-imidazole-coumarin structure | | Midkine (H441) |
| | | | Actin (H441) |
| 9 | (4-CF3-benzyl)-thiazolo-imidazole-coumarin structure | | Midkine (H441) |
| | | | Actin (H441) |
| 10 | (4-F-benzyl)-thiazolo-imidazole-(4-methoxyphenyl) structure | | Midkine (H441) |
| | | | Actin (H441) |

FIG. 8B

METHODS AND COMPOSITIONS TO TREAT CANCER

RELATED APPLICATIONS

This application is a division of U.S. application Ser. No. 14/897,539 filed Dec. 10, 2015 which is the U.S. National Phase of Application No. PCT/US2014/043029 entitled "METHODS AND COMPOSITIONS TO TREAT CANCER" filed Jun. 18, 2014, and published in English on Dec. 24, 2014 as WO 2014/205132 which claims the benefit of U.S. Provisional Application No. 61/837,436 filed Jun. 20, 2013 entitled "METHODS AND COMPOSITIONS TO TREAT CANCER" which are each incorporated herein by reference in its entirety.

FIELD OF THE INVENTION

Embodiments provided herein relate to methods and compositions for treating cancer. Some embodiments include treating lung cancers and renal cancers.

BACKGROUND OF THE INVENTION

Lung cancer is the leading cause of cancer-related mortality worldwide (Jemal A, et al., CA-Cancer J. Clin. 2011; 61:69-90; and Ferlay J, et al. Int. J. Cancer 2010; 127:2893-917.). Conventional chemotherapeutic regimens target lung cancer cells but also normal proliferating cells. Presently, survival following conventional chemotherapy of lung adenocarcinoma, the most frequent type of lung cancer, provides less than one-year median survival from the time of diagnosis (Schiller J H, et al. N. Engl. J. Med. 2002; 346:92-8). Molecular pathway-specific therapies for lung adenocarcinoma, e.g., targeting mutant EGFR or ALK fusions, limit non-tumor toxicity and extend survival time compared to the conventional chemotherapies (Choi Y L, et al., N. Engl. J. Med. 2010; 363:1734-9; Zakowski M F, et al., N. Engl. J. Med. 2006; 355:213-5; and Takeuchi K, et al., Nat. Med. 2012; 18:378-81). However, there is no targeted therapy for mutant KRAS-driven lung adenocarcinoma, one of the most frequent type of lung adenocarcinoma. Moreover, effective targeted therapies have been developed for adenocarcinomas but not squamous cell carcinomas. Therefore, specific therapies that target various lung tumor types are needed (Heist R S, et al., J. Thorac. Oncol. 2012; 7:924-33; Perez-Moreno P, et al., Clin. Cancer Res. 2012; 18:2443-51; and Ayoola A, et al., Cancer Invest. 2012; 30:433-46).

SUMMARY OF INVENTION

Some embodiments of the composition and methods provided herein include a pharmaceutical composition comprising a compound of formula (I) and a pharmaceutical carrier, wherein formula (I) is:

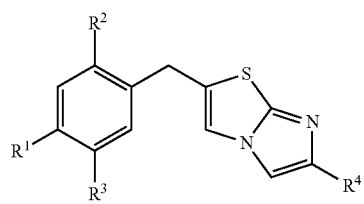

(I)

or a pharmaceutically acceptable salt thereof, wherein: $R^1$ is hydrogen, $-OCH_3$, $-CH_3$, $-CF_3$ or halogen; $R^2$ is hydrogen or chlorine; $R^3$ is hydrogen, chlorine or $-CF_3$; and $R^4$ is

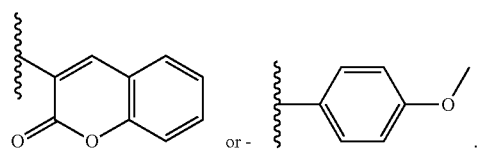

In some embodiments, $R^1$ is hydrogen or halogen; $R^2$ is hydrogen or chlorine; $R^3$ is hydrogen or chlorine, when $R^1$ is hydrogen then $R^2$ and $R^3$ are chlorine, and when $R^2$ and $R^3$ are chlorine then $R^1$ is hydrogen. In some embodiments, $R^1$ is selected from hydrogen, $-OCH_3$ and halogen; and $R^2$ and $R^3$ are hydrogen. In some embodiments, $R^1$ is fluorine.

In some embodiments, formula (I) is selected from the group consisting of:

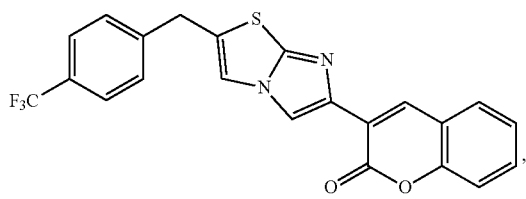

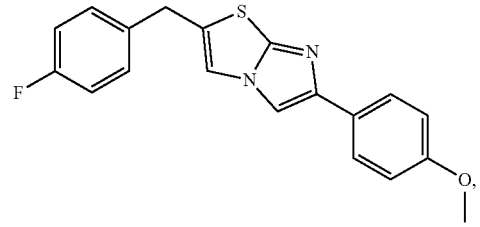

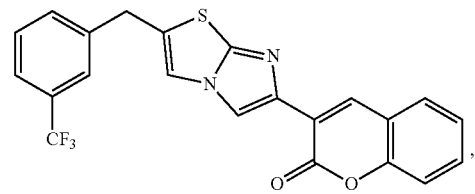

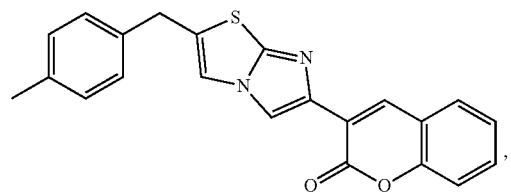

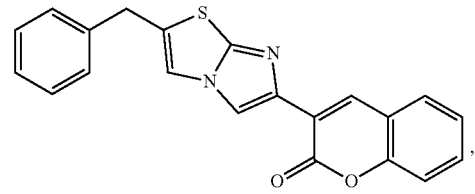

-continued

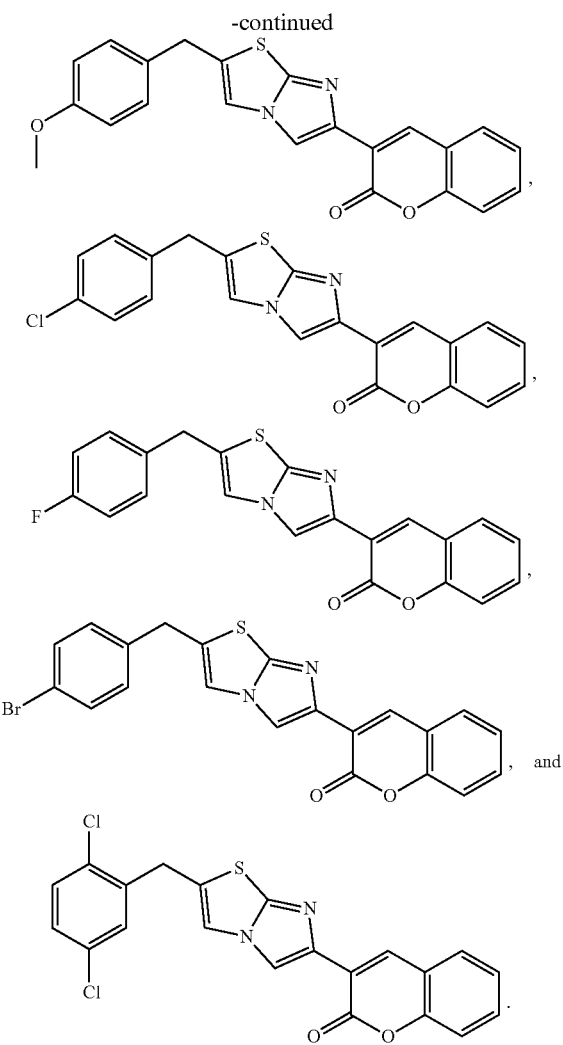

In some embodiments, formula (I) is:

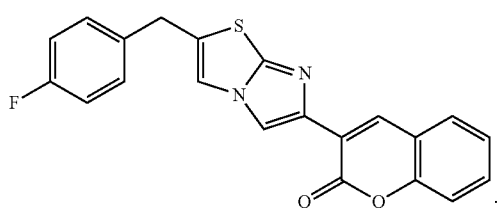

Some embodiments include a method of treating a subject having a disorder, comprising: administering an effective amount of a compound to a subject in need thereof, wherein the compound comprises formula (I):

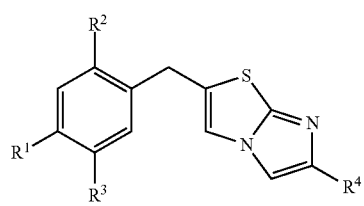

(I)

or a pharmaceutically acceptable salt thereof, wherein: $R^1$ is hydrogen, —$OCH_3$, —$CH_3$, —$CF_3$ or halogen; $R^2$ is hydrogen or chlorine; $R^3$ is hydrogen, chlorine or —$CF_3$; and
$R^4$ is

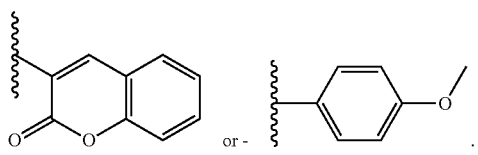

In some embodiments, $R^1$ is hydrogen or halogen; $R^2$ is hydrogen or chlorine; $R^3$ is hydrogen or chlorine, when $R^1$ is hydrogen then $R^2$ and $R^3$ are chlorine, and when $R^2$ and $R^3$ are chlorine then $R^1$ is hydrogen. In some embodiments, $R^1$ is selected from hydrogen, —$OCH_3$ and halogen; and $R^2$ and $R^3$ are hydrogen. In some embodiments, $R^1$ is fluorine.

In some embodiments, formula (I) is selected from the group consisting of:

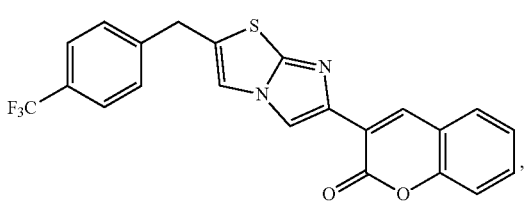

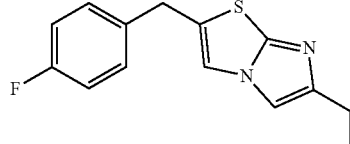

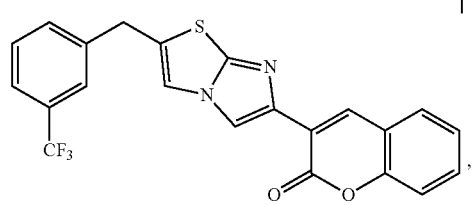

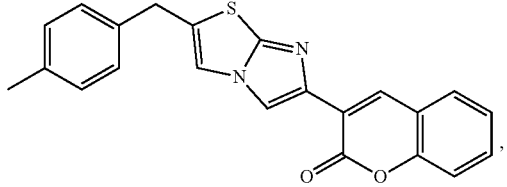

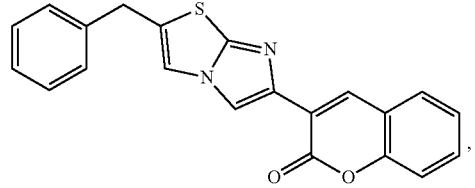

-continued

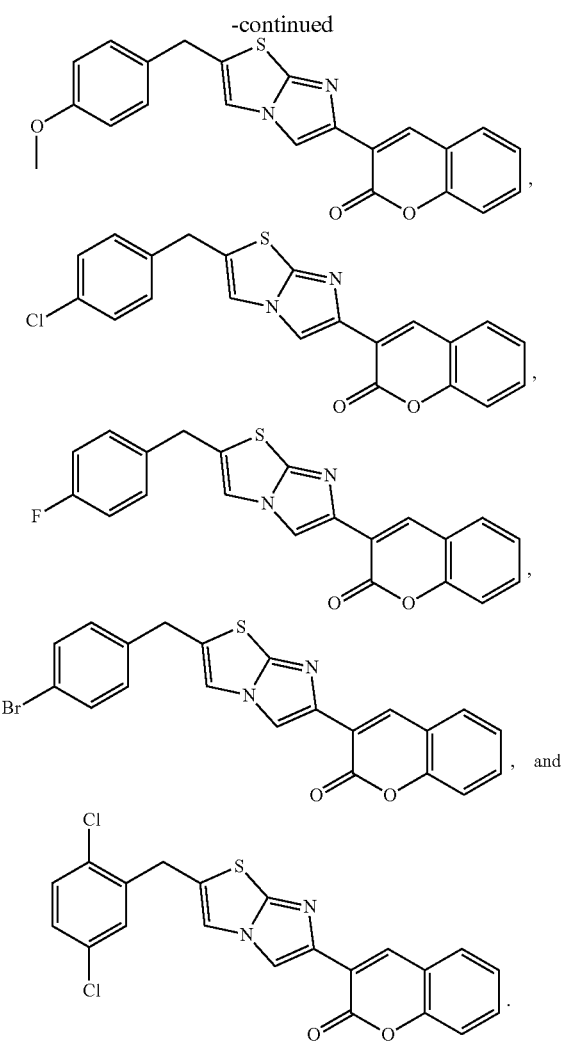

In some embodiments, formula (I) is:

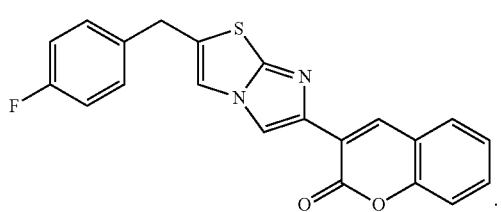

In some embodiments, the disorder is selected from the group consisting of lung cancer, renal cancer, and an inflammatory disorder. In some embodiments, the lung cancer is selected from the group consisting of squamous cell carcinoma, and adenocarcinoma. In some embodiments, the inflammatory disorder is selected from the group consisting of rheumatoid arthritis, atherosclerosis, and restenosis. In some embodiments, the subject is mammalian. In some embodiments, the subject is human.

Some embodiments include a method of inhibiting a neoplastic cell, comprising contacting the cell with an amount of a formula (I) sufficient to inhibit the cell, wherein formula (I) is:

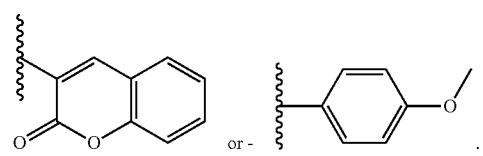

or a pharmaceutically acceptable salt thereof, wherein: $R^1$ is hydrogen, —$OCH_3$, —$CH_3$, —$CF_3$ or halogen; $R^2$ is hydrogen or chlorine; $R^3$ is hydrogen, chlorine or —$CF_3$; and $R^4$ is

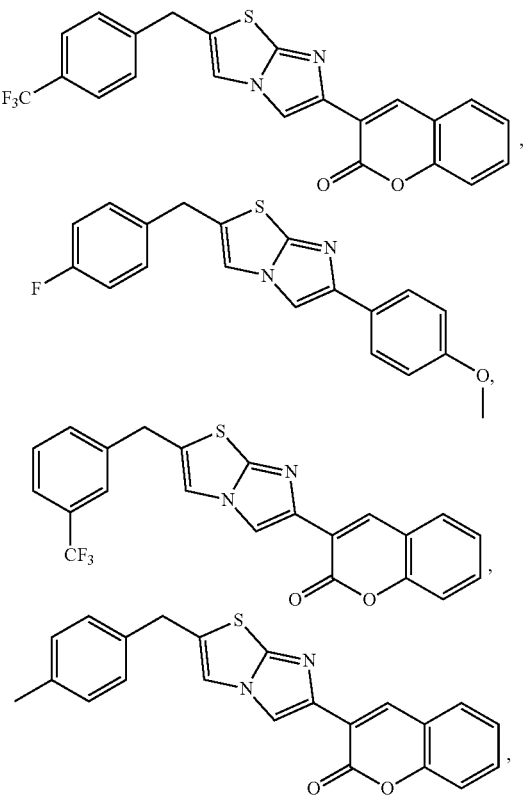

In some embodiments, $R^1$ is hydrogen or halogen; $R^2$ is hydrogen or chlorine; $R^3$ is hydrogen or chlorine, when $R^1$ is hydrogen then $R^2$ and $R^3$ are chlorine, and when $R^2$ and $R^3$ are chlorine then $R^1$ is hydrogen. In some embodiments, $R^1$ is selected from hydrogen, —$OCH_3$ and halogen; and $R^2$ and $R^3$ are hydrogen. In some embodiments, $R^1$ is fluorine.

In some embodiments, formula (I) is selected from the group consisting of:

-continued

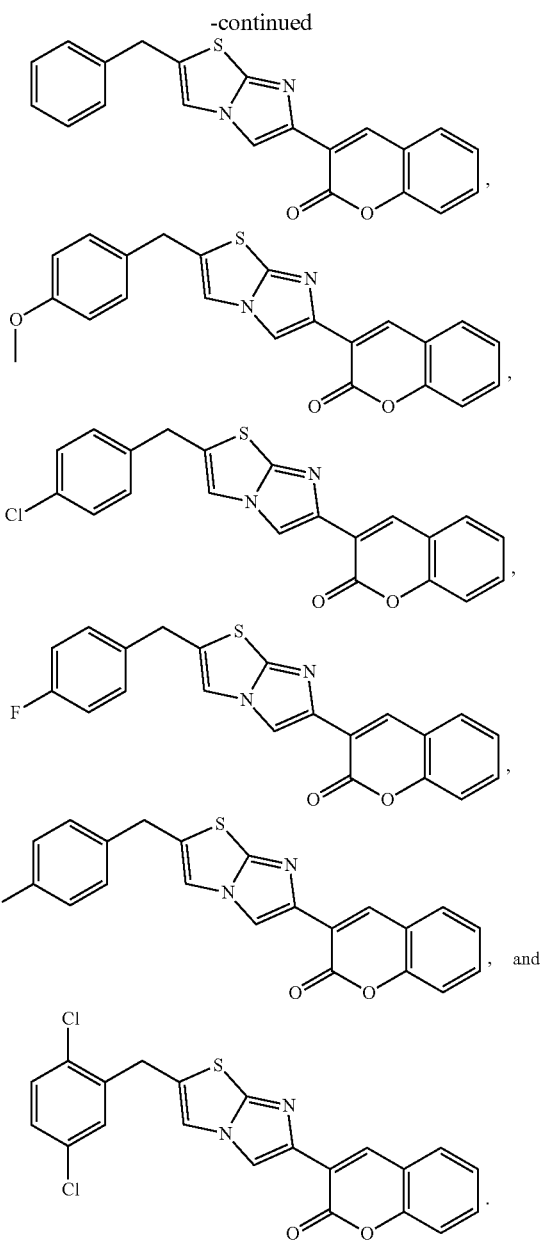

, and

In some embodiments, formula (I) is:

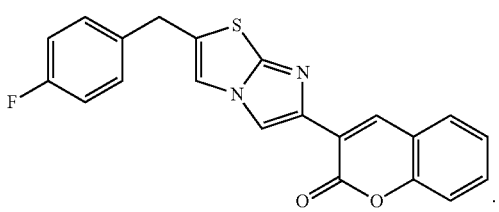

In some embodiments, the cell is ex vivo. In some embodiments, the cell is in vivo. In some embodiments, the cell is a lung cell. In some embodiments, the cell is from a tumor selected from the group consisting of squamous cell carcinoma, and adenocarcinoma In some embodiments, the cell is mammalian. In some embodiments, the cell is human.

Some embodiments include a compound for use in treating a subject having a disorder, wherein the compound comprises formula (I):

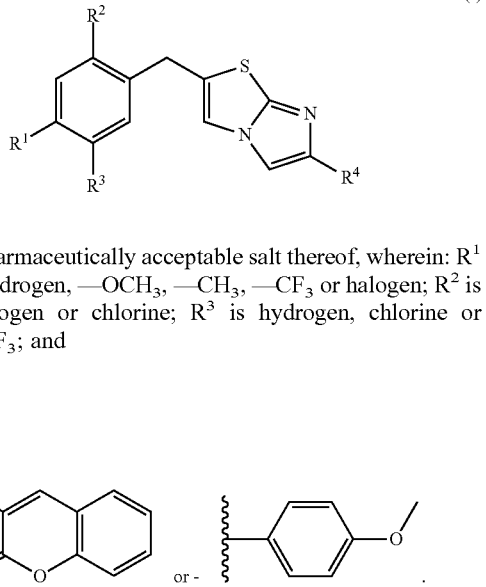

or a pharmaceutically acceptable salt thereof, wherein: $R^1$ is hydrogen, —$OCH_3$, —$CH_3$, —$CF_3$ or halogen; $R^2$ is hydrogen or chlorine; $R^3$ is hydrogen, chlorine or —$CF_3$; and $R^4$ is

[structure] or - [structure].

In some embodiments, $R^1$ is hydrogen or halogen; $R^2$ is hydrogen or chlorine; $R^3$ is hydrogen or chlorine, when $R^1$ is hydrogen then $R^2$ and $R^3$ are chlorine, and when $R^2$ and $R^3$ are chlorine then $R^1$ is hydrogen. In some embodiments, $R^1$ is selected from hydrogen, —$OCH_3$ and halogen; and $R^2$ and $R^3$ are hydrogen. In some embodiments, $R^1$ is fluorine.

In some embodiments, formula (I) is selected from the group consisting of:

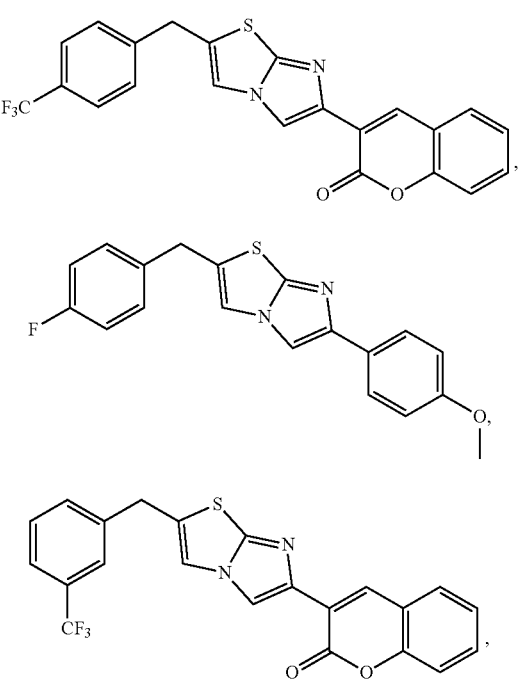

-continued

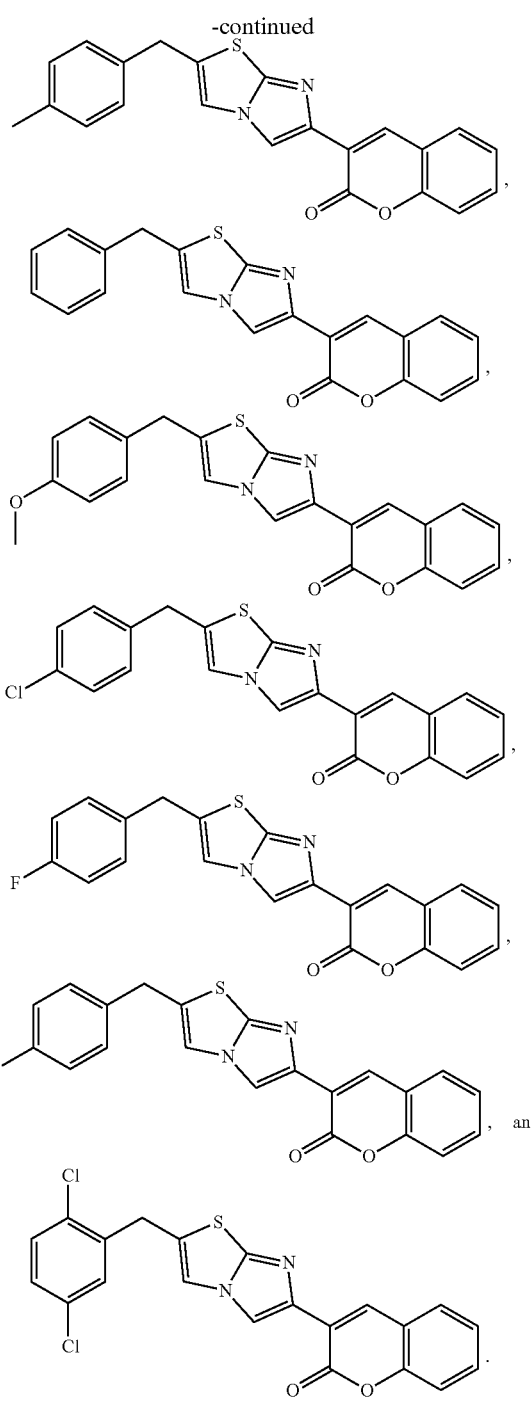

In some embodiments, formula (I) is:

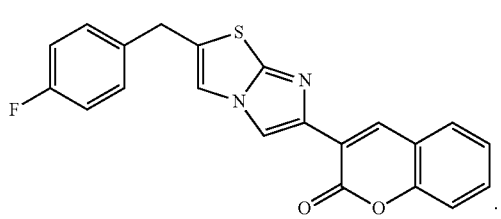

In some embodiments, the disorder is selected from the group consisting of lung cancer, renal cancer, and an inflammatory disorder. In some embodiments, the lung cancer is selected from the group consisting of squamous cell carcinoma, and adenocarcinoma. In some embodiments, the inflammatory disorder is selected from the group consisting of rheumatoid arthritis, atherosclerosis, and restenosis.

In some embodiments, the compound of formula (I) has the structure of formula (II):

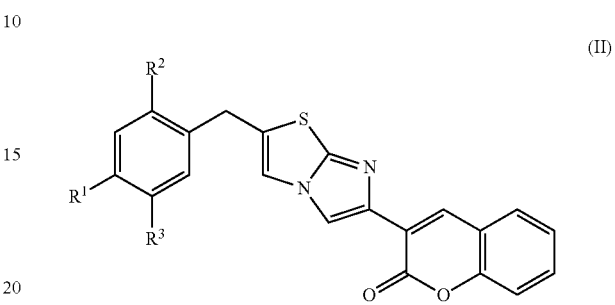

or a pharmaceutically acceptable salt thereof, wherein: $R^1$ is hydrogen, —$OCH_3$, or halogen; $R^2$ is hydrogen or chlorine; $R^3$ is hydrogen or chlorine.

In some embodiments, formula (I) has the structure of formula (II):

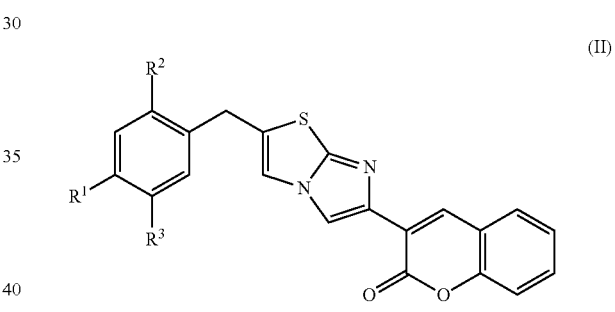

or a pharmaceutically acceptable salt thereof, wherein: $R^1$ is hydrogen, —$OCH_3$, or halogen; $R^2$ is hydrogen or chlorine; $R^3$ is hydrogen or chlorine.

In some embodiments, formula (I) has the structure of formula (II):

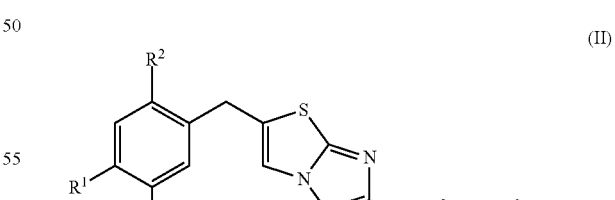

or a pharmaceutically acceptable salt thereof, wherein: $R^1$ is hydrogen, —$OCH_3$, or halogen; $R^2$ is hydrogen or chlorine; $R^3$ is hydrogen or chlorine.

In some embodiments, formula (I) has the structure of formula (II):

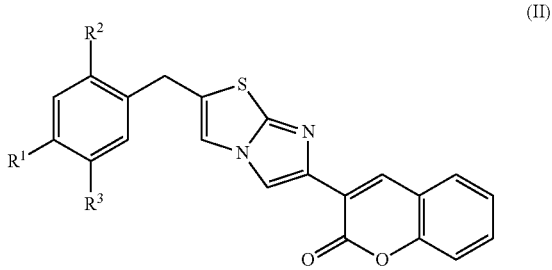

(II)

or a pharmaceutically acceptable salt thereof, wherein: $R^1$ is hydrogen, —$OCH_3$, or halogen; $R^2$ is hydrogen or chlorine; $R^3$ is hydrogen or chlorine.

Some embodiments include use of any one of the foregoing compounds to treat a disorder selected from the group consisting of lung cancer, renal cancer, and an inflammatory disorder. In some embodiments, the lung cancer is selected from the group consisting of squamous cell carcinoma, and adenocarcinoma. In some embodiments, the inflammatory disorder is selected from the group consisting of rheumatoid arthritis, atherosclerosis, and restenosis.

Some embodiments include use of any one of the foregoing compounds in the manufacture of a medicament to treat a disorder selected from the group consisting of lung cancer, renal cancer, and an inflammatory disorder. In some embodiments, the lung cancer is selected from the group consisting of squamous cell carcinoma, and adenocarcinoma. In some embodiments, the inflammatory disorder is selected from the group consisting of rheumatoid arthritis, atherosclerosis, and restenosis.

BRIEF DESCRIPTION OF THE DRAWINGS

FIG. 2A depicts an immunoblot analysis of MDK in indicated cells with the expression level of actin as control. FIG. 2B depicts an immunoblot confirming MDK knockdown with anti-MDK siRNA in H441 lung adenocarcinoma cells. FIG. 2C depicts a trypan blue exclusion assay demonstrating that MDK knockdown resulted in decreased cell proliferation of H441 lung adenocarcinoma cells. Statistical significance was defined as P<0.01.

FIG. 3A depicts the structure of iMDK. FIG. 3B depicts an immunoblot analysis demonstrating that iMDK dose-dependently inhibited MDK expression but did not suppress VEGF expression in H441 lung adenocarcinoma cells 48 hours after the treatment. Actin is shown as a control.

FIG. 4A depicts cells were plated in 24-well plates at a density of 1×10⁵ cells 24 hours before iMDK treatment. Cell viability was evaluated 48 hours after the treatment. Statistical significance was defined as P<0.01. FIG. 4B depicts phase-contrast photomicrographs of H441 cells after iMDK treatment. Cell morphology was evaluated 48 hours after the treatment. Photomicrographs were taken at a magnification of 100×.

FIG. 5A depict morphological analysis of H441 cells treated with iMDK. Hoechst staining demonstrated that iMDK dose-dependently increased apoptosis in H441 lung adenocarcinoma cells. Cells were treated with indicated concentration of iMDK for 72 hours and stained with Hoechst 33342 dye and analyzed under a fluorescence microscope. FIG. 5B depicts flow cytometric analysis of apoptosis induced by iMDK. Cells were treated with iMDK for 72 hours and sub-G0/G1 DNA content was measured by propidium iodide stain and flow cytometric analysis. FIG. 5C depicts H441 lung adenocarcinoma cells showing increased caspase-3 processing following iMDK treatment. Cell lines were treated for 48 hours with iMDK in indicated concentrations and harvesting for immunoblot analysis.

FIG. 6A depicts the activation of PI3K, AKT, and the expression of IAP family members, survivin and XIAP, were suppressed by iMDK treatment in a dose-dependent manner. Significantly, BAD expression was increased after the treatment. FIG. 6B depicts iMDK suppressed the activation of PI3K, AKT and expression of survivin and XIAP. BAD was significantly increased after the treatment at a concentration of 50 nM.

FIG. 7A depicts suppression of tumor growth by intraperitoneal administration. Volume of the tumors derived from H441 lung adenocarcinoma cells treated with either DMSO (control), iMDK 3 times/week or iMDK 5 times/week is shown. The volume was monitored over time (days) after inoculation of tumor cells. Eight mice were studied in each group. Tumor growth is expressed as mean tumor volume; bars represent SD. Statistical significance was defined as P<0.01. FIG. 7B depicts suppression of tumor growth of H441 subcutaneous xenografts by intraperitoneal administration of iMDK (9 mg/kg). On day 10, all of the mice were sacrificed and tumors imaged. Shown are data from a typical experiment.

FIG. 8A-8B depict Western blots of midkine expression in H441 cells treated with various compounds.

DETAILED DESCRIPTION

Figure 1A:
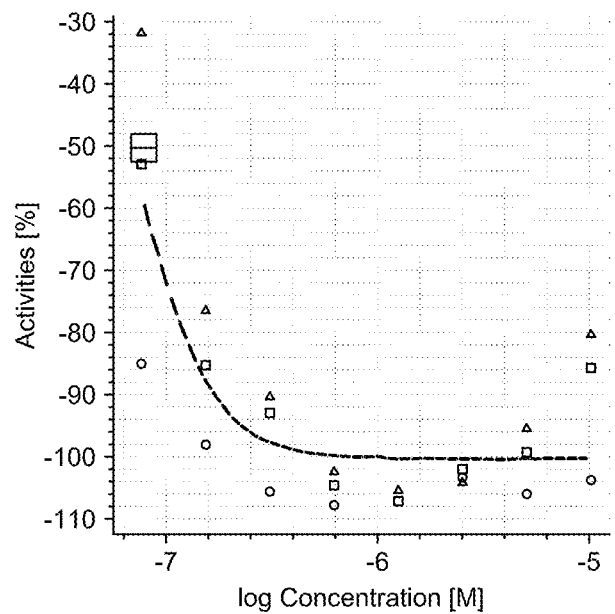
FIG. 1A-1D depict dose response curves for example compounds, 1, 2, 3, and 4, respectively.
Figure 1B:
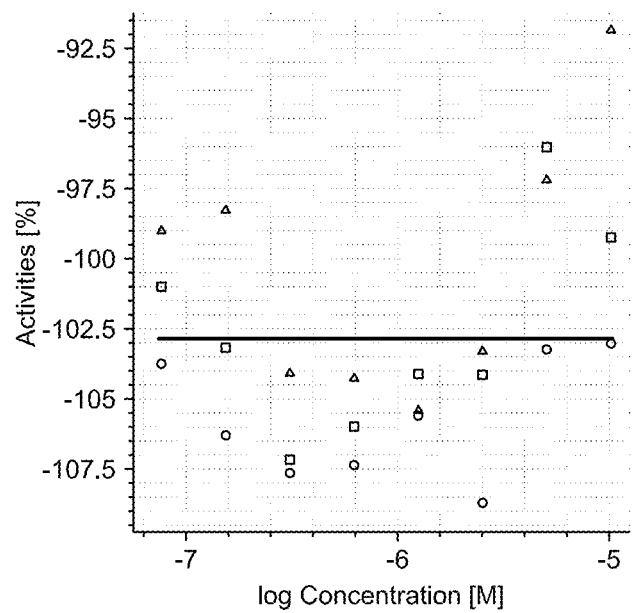
Figure 1C:
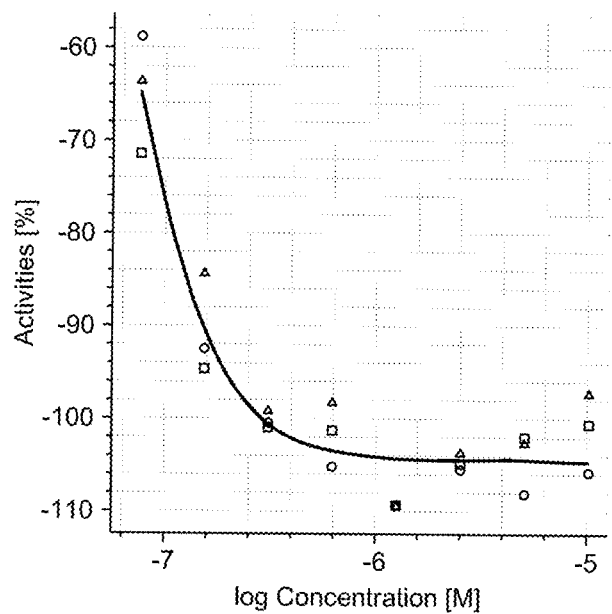
Figure 1D:
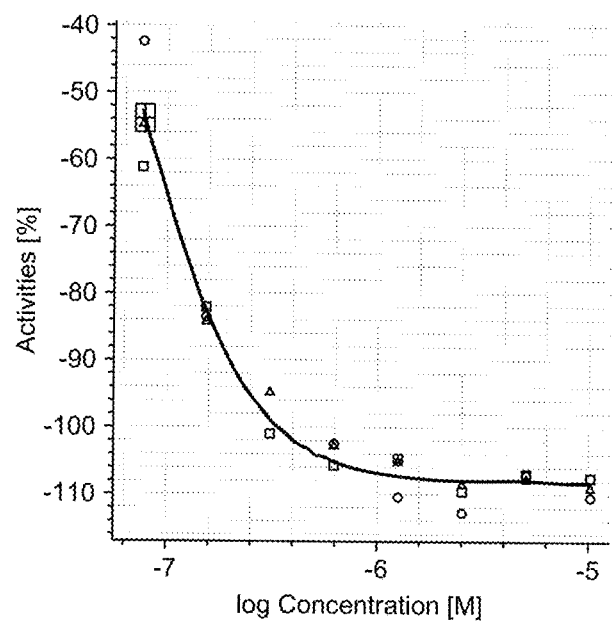

Midkine (MDK) is a heparin-binding growth factor that is highly expressed in many malignant tumors, including lung, esophageal, stomach, colon, hepatocellular, breast, renal and pancreatic carcinoma (Tomizawa M, et al., Br. J. Cancer 2003; 89:1086-90; Takei Y, et al., J. Biol. Chem. 2002; 277:23800-6; Shimada H, et al., Cancer Science. 2003; 94:628-32; Miyauchi M, et al., Int. J. Cancer. 2001; 91:723-7; Ikematsu S, et al., Br. J. Cancer 2000; 83:701-6; Tsutsui J, et al., Cancer Res. 1993; 53:1281-5). MDK binds to multiple membrane receptors, ALK, syndecans, PTP and LRP, and subsequently activates PI3 kinase (PI3K) and MAP kinase pathways that induce cell proliferation and enhance angiogenic and anti-apoptotic activities (Owada K, et al., J. Neurochem. 1999; 73:2084-92; Muramatsu T. J. Biochem. 2002; 132:359-71). Inhibition of MDK by siRNA suppresses cell growth of cancer cells that express MDK, indicating that MDK might be a potential target for lung cancer therapy (Jin Z, et al., Clin. Cancer Res. 2008; 14:5033-42). Since mice lacking the Mdk gene are viable, targeting MDK is an attractive therapeutic approach since its inhibition is unlikely to have systemic deleterious effects (Ezquerra L, et al., Biochem. Biophys. Res. Commun. 2005; 333:636-43). The recognition of the potential role of the MDK pathway in the treatment of cancer has increased efforts to identify MDK inhibitors. Matsui et al. identified synthetic peptides and compounds that inhibit MDK-mediated cell migration in vitro; however, these proved not to be potent and lack clinical utility (Matsui T, et al., Int. Arch. Med. 2010; 3:12).

Embodiments relate to a low molecular weight compound (iMDK) that suppressed endogenous MDK expression. iMDK inhibited the cell growth of MDK-positive H441 lung adenocarcinoma cells that harbor an oncogenic KRAS mutation and H520 squamous cell lung cancer cells, both of which are types of untreatable lung cancer. However, the compound did not reduce the cell viability of MDK-negative A549 lung adenocarcinoma cells or normal human lung fibroblast (NHLF) indicating its specificity. iMDK suppressed the endogenous expression of MDK but not VEGF, another growth factor. While not being bound by any particular theory, iMDK appears to suppress the growth of H441 cells by inhibiting the PI3K pathway and inducing apoptosis. Systemic administration of iMDK significantly inhibited tumor growth in a xenograft mouse model in vivo. Inhibition of MDK with iMDK provides a therapeutic approach for the treatment of lung cancers that are driven by MDK.

Small Molecule Inhibitors

Some embodiments of the compositions and methods provided herein include the use of small molecules having activity to inhibit expression of MDK. Examples of such small molecules include formula (I):

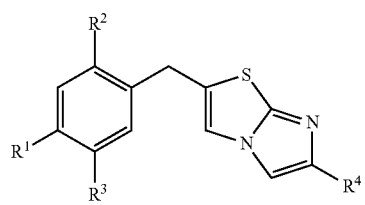

or a pharmaceutically acceptable salt thereof, wherein:
$R^1$ is hydrogen, —OCH$_3$, —CH$_3$, —CF$_3$ or halogen;
$R^2$ is hydrogen or chlorine;
$R^3$ is hydrogen, chlorine or —CF$_3$; and
$R^4$ is

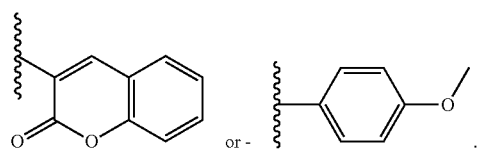

In some, embodiments, $R^1$ is hydrogen or halogen; $R^2$ is hydrogen or chlorine; $R^3$ is hydrogen or chlorine, when $R^1$ is hydrogen then $R^2$ and $R^3$ are chlorine, and when $R^2$ and $R^3$ are chlorine then $R^1$ is hydrogen.

In some, embodiments, $R^1$ is selected from hydrogen, —OCH$_3$ and halogen; and $R^2$ and $R^3$ are hydrogen.

In some, embodiments, $R^1$ is fluorine.

In some, embodiments, formula (I) is selected from the group consisting of:

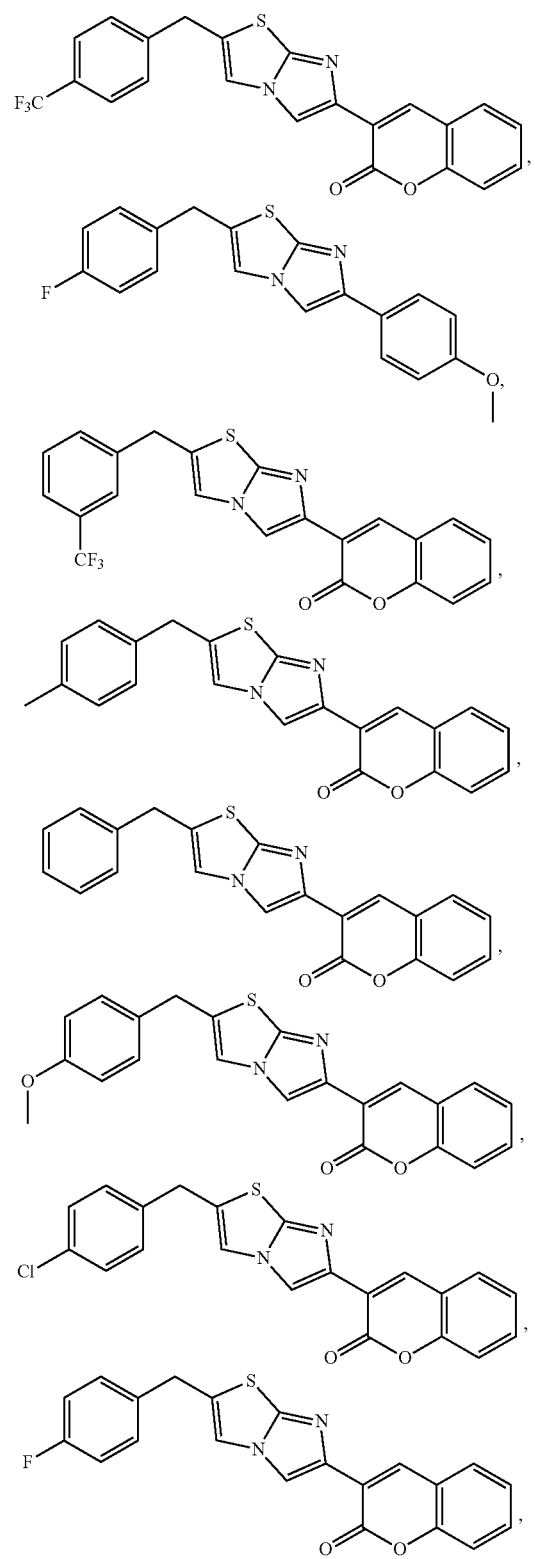

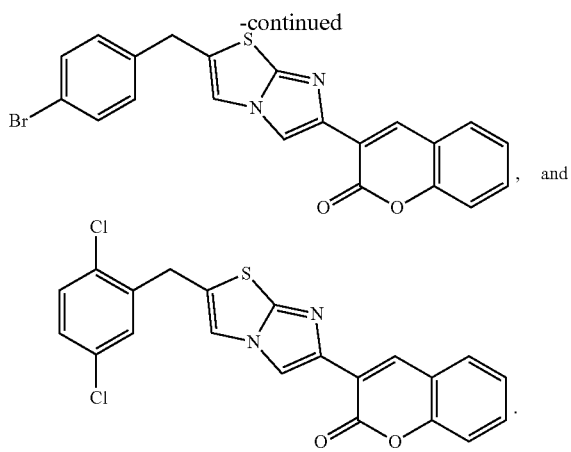

In some, embodiments, formula (I) is:

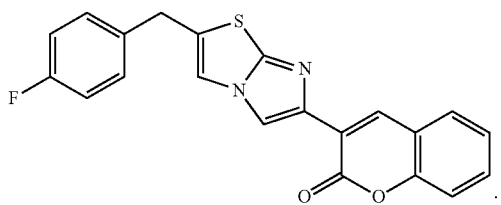 [SMILES: O=c1oc2ccccc2cc1-c1cn2cc(Cc3ccc(F)cc3)sc2n1]

In some embodiments, the compound of formula (I) has the structure of formula (II):

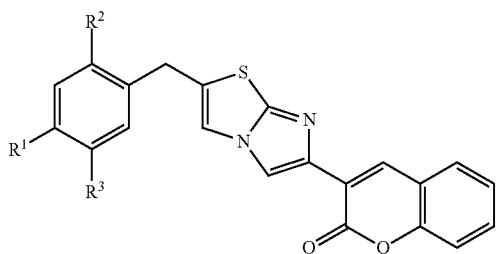

or a pharmaceutically acceptable salt thereof,
wherein:
$R^1$ is hydrogen, —$OCH_3$, or halogen;
$R^2$ is hydrogen or chlorine;
$R^3$ is hydrogen or chlorine.

Pharmaceutical Compositions

In some embodiments, small molecules provided herein may be administered in an intravenous or subcutaneous unit dosage form; however, other routes of administration are also contemplated. Contemplated routes of administration include but are not limited to oral, parenteral, intravenous, and subcutaneous. In some embodiments, small molecules provided herein can be formulated into liquid preparations for, e.g., oral administration. Suitable forms include suspensions, syrups, elixirs, and the like. In some embodiments, unit dosage forms for oral administration include tablets and capsules. Unit dosage forms configured for administration once a day; however, in certain embodiments it can be desirable to configure the unit dosage form for administration twice a day, or more.

In some embodiments, pharmaceutical compositions are isotonic with the blood or other body fluid of the recipient. The isotonicity of the compositions can be attained using sodium tartrate, propylene glycol or other inorganic or organic solutes. An example includes sodium chloride. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the pharmaceutical compositions can be maintained at the selected level using a pharmaceutically acceptable thickening agent. Methylcellulose is useful because it is readily and economically available and is easy to work with. Other suitable thickening agents include, for example, xanthan gum, carboxymethyl cellulose, hydroxypropyl cellulose, carbomer, and the like. In some embodiments, the concentration of the thickener will depend upon the thickening agent selected. An amount can be used that will achieve the selected viscosity. Viscous compositions are normally prepared from solutions by the addition of such thickening agents.

A pharmaceutically acceptable preservative can be employed to increase the shelf life of the pharmaceutical compositions. Benzyl alcohol can be suitable, although a variety of preservatives including, for example, parabens, thimerosal, chlorobutanol, or benzalkonium chloride can also be employed. A suitable concentration of the preservative is typically from about 0.02% to about 2% based on the total weight of the composition, although larger or smaller amounts can be desirable depending upon the agent selected. Reducing agents, as described above, can be advantageously used to maintain good shelf life of the formulation.

In some embodiments, small molecules provided herein can be in admixture with a suitable carrier, diluent, or excipient such as sterile water, physiological saline, glucose, or the like, and can contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; $18^{th}$ and $19^{th}$ editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions can be provided as a tablet, aqueous or oil suspension, dispersible powder or granule, emulsion, hard or soft capsule, syrup or elixir. Compositions intended for oral use can be prepared according to any method known in the art for the manufacture of pharmaceutical compositions and can include one or more of the following agents: sweeteners, flavoring agents, coloring agents and preservatives. Aqueous suspensions can contain the active ingredient in admixture with excipients suitable for the manufacture of aqueous suspensions.

Formulations for oral use can also be provided as hard gelatin capsules, wherein the active ingredient(s) are mixed with an inert solid diluent, such as calcium carbonate, calcium phosphate, or kaolin, or as soft gelatin capsules. In soft capsules, the inhibitors can be dissolved or suspended in suitable liquids, such as water or an oil medium, such as peanut oil, olive oil, fatty oils, liquid paraffin, or liquid polyethylene glycols. Stabilizers and microspheres formulated for oral administration can also be used. Capsules can include push-fit capsules made of gelatin, as well as soft, sealed capsules made of gelatin and a plasticizer, such as glycerol or sorbitol. The push-fit capsules can contain the active ingredient in admixture with fillers such as lactose, binders such as starches, and/or lubricants such as talc or magnesium stearate and, optionally, stabilizers.

Tablets can be uncoated or coated by known methods to delay disintegration and absorption in the gastrointestinal tract and thereby provide a sustained action over a longer period of time. For example, a time delay material such as glyceryl monostearate can be used. When administered in solid form, such as tablet form, the solid form typically comprises from about 0.001 wt. % or less to about 50 wt. % or more of active ingredient(s), for example, from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Tablets can contain the active ingredients in admixture with non-toxic pharmaceutically acceptable excipients including inert materials. For example, a tablet can be prepared by compression or molding, optionally, with one or more additional ingredients. Compressed tablets can be prepared by compressing in a suitable machine the active ingredients in a free-flowing form such as powder or granules, optionally mixed with a binder, lubricant, inert diluent, surface active or dispersing agent. Molded tablets can be made by molding, in a suitable machine, a mixture of the powdered inhibitor moistened with an inert liquid diluent.

In some embodiments, each tablet or capsule contains from about 1 mg or less to about 1,000 mg or more of a small molecule provided herein, for example, from about 10, 20, 30, 40, 50, 60, 70, 80, 90, or 100 mg to about 150, 200, 250, 300, 350, 400, 450, 500, 550, 600, 650, 700, 750, 800, or 900 mg. In some embodiments, tablets or capsules are provided in a range of dosages to permit divided dosages to be administered. A dosage appropriate to the patient and the number of doses to be administered daily can thus be conveniently selected. In certain embodiments two or more of the therapeutic agents can be incorporated to be administered into a single tablet or other dosage form (e.g., in a combination therapy); however, in other embodiments the therapeutic agents can be provided in separate dosage forms.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents can be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya or tragacanth, or alginic acid or salts thereof.

Binders can be used to form a hard tablet. Binders include materials from natural products such as acacia, tragacanth, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, can be included in tablet formulations.

Surfactants can also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Controlled release formulations can be employed wherein the amifostine or analog(s) thereof is incorporated into an inert matrix that permits release by either diffusion or leaching mechanisms. Slowly degenerating matrices can also be incorporated into the formulation. Other delivery systems can include timed release, delayed release, or sustained release delivery systems.

Coatings can be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments can be added for identification or to characterize different combinations of inhibitor doses.

When administered orally in liquid form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

Pulmonary delivery of the inhibitor can also be employed. The inhibitor is delivered to the lungs while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of inhibitor. Typically, each formulation is specific to the type of device employed and can involve the use of an appropriate propellant material, in addition to diluents, adjuvants, and/or carriers useful in therapy.

The inhibitor and/or other optional active ingredients are advantageously prepared for pulmonary delivery in particulate form with an average particle size of from 0.1 µm or less to 10 µm or more, for example, from about 0.2, 0.3, 0.4, 0.5, 0.6, 0.7, 0.8, or 0.9 µm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 µm. Pharmaceutically acceptable carriers for pulmonary delivery of inhibitor include carbohydrates such as trehalose, mannitol, xylitol, sucrose, lactose, and sorbitol. Other ingredients for use in formulations can include DPPC, DOPE, DSPC, and DOPC. Natural or synthetic surfactants can be used, including polyethylene glycol and dextrans, such as cyclodextran. Bile salts and other related enhancers, as well as cellulose and cellulose derivatives, and amino acids can also be used. Liposomes, microcapsules, microspheres, inclusion complexes, and other types of carriers can also be employed.

Pharmaceutical formulations suitable for use with a nebulizer, either jet or ultrasonic, typically comprise the inhibitor dissolved or suspended in water at a concentration of about 0.01 or less to 100 mg or more of inhibitor per mL of solution, for example, from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg per mL of solution. The formulation can also include a buffer and a simple sugar (e.g., for protein stabilization and regulation of osmotic pressure). The nebulizer formulation can also contain a surfactant, to reduce or prevent surface induced aggregation of the inhibitor caused by atomization of the solution in forming the aerosol.

Formulations for use with a metered-dose inhaler device generally comprise a finely divided powder containing the active ingredients suspended in a propellant with the aid of a surfactant. The propellant can include conventional propellants, such as chlorofluorocarbons, hydrochlorofluorocarbons, hydrofluorocarbons, and hydrocarbons. Example propellants include trichlorofluoromethane, dichlorodifluoromethane, dichlorotetrafluoroethanol, 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing inhibitor, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, for example, from about 5, 10, 15, 20, 25, 30, 35, 40, 45, or 50 wt. % to about 55, 60, 65, 70, 75, 80, 85, or 90 wt. % of the formulation.

In some embodiments, a small molecule provided herein can be administered by intravenous, parenteral, or other injection, in the form of a pyrogen-free, parenterally acceptable aqueous solution or oleaginous suspension. Suspensions can be formulated according to methods well known in the art using suitable dispersing or wetting agents and suspending agents. The preparation of acceptable aqueous solutions with suitable pH, isotonicity, stability, and the like, is within the skill in the art. In some embodiments, a pharmaceutical composition for injection can include an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils can be employed conventionally as a solvent or suspending medium. For this purpose, any bland fixed oil can be employed including synthetic mono or diglycerides. In addition, fatty acids such as oleic acid can likewise be used in the formation of injectable preparations. The pharmaceutical compositions can also contain stabilizers, preservatives, buffers, antioxidants, or other additives known to those of skill in the art.

The duration of the injection can be adjusted depending upon various factors, and can comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

In some embodiments, small molecules provided herein can additionally employ adjunct components conventionally found in pharmaceutical compositions in their art-established fashion and at their art-established levels. Thus, for example, the compositions can contain additional compatible pharmaceutically active materials for combination therapy (such as supplementary antimicrobials, antipruritics, astringents, local anesthetics, anti-inflammatory agents, reducing agents, chemotherapeutics and the like), or can contain materials useful in physically formulating various dosage forms, such as excipients, dyes, thickening agents, stabilizers, preservatives or antioxidants. Anti-cancer agents that can be used in combination with the small molecules provided herein include vinca alkaloids such as vinblastine and vincristine; anthracyclines such as doxorubicin, daunorubicin, epirubicin; anthracenes such as bisantrene and mitoxantrone; epipodophyllo-toxins such as etoposide and teniposide; and other anticancer drugs such as actinomyocin D, mithomycin C, mitramycin, methotrexate, docetaxel, etoposide (VP-16), paclitaxel, docetaxel, and adriamycin); and immunosuppressants (e.g., cyclosporine A, tacrolimus).

In some embodiments, the small molecules provided herein can be provided to an administering physician or other health care professional in the form of a kit. The kit is a package which houses a container which contains the inhibitor(s) in a suitable pharmaceutical composition, and instructions for administering the pharmaceutical composition to a subject. The kit can optionally also contain one or more additional therapeutic agents, e.g., chemotherapeutics currently employed for treating the sarcomas described herein. For example, a kit containing one or more compositions comprising small molecules provided herein in combination with one or more additional chemotherapeutic agents can be provided, or separate pharmaceutical compositions containing a small molecule provided herein and additional therapeutic agents can be provided. The kit can also contain separate doses of a small molecule provided herein for serial or sequential administration. The kit can optionally contain one or more diagnostic tools and instructions for use. The kit can contain suitable delivery devices, e.g., syringes, and the like, along with instructions for administering the inhibitor(s) and any other therapeutic agent. The kit can optionally contain instructions for storage, reconstitution (if applicable), and administration of any or all therapeutic agents included. The kits can include a plurality of containers reflecting the number of administrations to be given to a subject.

EXAMPLES

Example 1—Screening Test Compounds

A library of compounds was screened for activity to reduce expression of midkine in vitro. HEK293 cells were stably transfected with the pGL4 vector comprising a midkine promoter coupled to a luciferase reporter gene. Midkine expression was upregulated by treating the cells with retinoic acid, and then treating the cells with a test compound. Changes in luciferase production were measured to access the inhibitory activity of the test compounds. The primary screen included 44,000 test compounds. Test compounds that reduced cell viability by more than 50% were eliminated from the screen. From the primary screen, 351 test compounds were further examined. From the secondary screen, 78 test compounds were examined using a dose-response assay, and the EC50 for the test compounds was determined. Example test compounds are listed in TABLE 1.

Cell Lines and Culture Conditions: the human pulmonary adenocarcinoma cells H322, H358, H441 and A549 and the human lung squamous cell carcinoma cells H520 were obtained from the American Type Culture Collection (Manassas, Va.) and grown in RPMI 1640 (H322, H358, H520) or high glucose Dulbecco's modified Eagle medium (H441, A549 cells) supplemented with 10% heat-inactivated fetal bovine serum. The human malignant mesothelioma cells ACC-MESO-1 (MESO-1) obtained from JCRB Cell Bank (Osaka, Japan) and the human lung squamous cell carcinoma cells SQ5 were grown in RPMI 1640 supplemented

TABLE 1

| Example compound No. | Structure | $EC_{50}$ (nM) | Lower 95% confidence limit (nM) | Upper 95% confidence limit (nM) |
| --- | --- | --- | --- | --- |
| 1 | [structure: 4-chlorobenzyl-imidazothiazole-chromenone] | 14.040 | 10.730 | 18.370 |
| 2 | [structure: 4-fluorobenzyl-imidazothiazole-chromenone] | | | |
| 3 | [structure: 4-bromobenzyl-imidazothiazole-chromenone] | 12.150 | 10.510 | 14.030 |
| 4 | [structure: 2,5-dichlorobenzyl-imidazothiazole-chromenone] | 15.910 | 14.530 | 17.410 |

Dose response curves for example compounds 1, 2, 3, and 4 are shown in FIGS. 1A, 1B, 1C, and 1D, respectively. Example compound 2 (iMDK) had exceptional activity and was examined further.

Example 2—In Vitro and In Vivo Analysis of iMDK

Materials and Methods

Reagents: 3-[2-(4-fluorobenzyl)imidazo[2,1-beta][1,3]thiazol-6-yl]-2H-chromen-2-one (iMDK) purchased from ChemDiv (San Diego, Calif.) was dissolved in DMSO.

with 10% heat-inactivated fetal bovine serum. The normal human lung fibroblasts (NHLF) obtained from Clonetics (San Diego, Calif.) were grown in high glucose Dulbecco's modified Eagle medium. All cell lines were cultured in 10% $CO_2$ at 37° C.

Immunoblot analysis: cells were lysed in ice-cold lysis buffer [1% Triton X-100, 20 mM Tris-HCl (pH 8.0), 137 mM NaCl, 10% glycerol (v/v), 2 mM EDTA, 1 mM sodium orthovanadate (v/v), 1 mM phenylmethylsulfonyl fluoride]. Cell lysates were clarified by centrifugation (10 min at 15,000×g at 4° C.) and protein concentration determined using the BCA protein assay (Thermo Fisher Scientific, Rockford, Ill.). Equal amounts of protein were separated on an SDS-PAGE gel. The gel was electrophoretically transferred to a Hybond PVDF transfer membrane (Amersham, Arlington Heights, Ill.) and incubated with primary and secondary antibodies according to the Supersignal® West Pico chemiluminescence protocol (Pierce, Rockford, Ill.). Antibody specific for β-actin antibody was obtained from Sigma (St. Louis, Mo.) and antibody specific for human MDK was obtained from Abcam (Cambridge, UK). Antibody specific for caspase-3, PI3 kinase p85, phosphorylated-PI3K p85 (Tyr458)/p55 (Tyr199), AKT, phosphorylated-AKT (Ser473), Bad, XIAP, survivin were obtained from Cell Signaling Technology (Beverly, Mass.). Antibody specific for VEGF was purchased from Santa Cruz Biotechnology (Santa Cruz, Calif.). Secondary horseradish peroxidase-conjugated antibodies were obtained from Jackson Immunoresearch Laboratories (West Grove, Pa.). Secondary horseradish peroxidase-conjugated antibodies were obtained from Jackson Immunoresearch Laboratories (West Grove, Pa.).

siRNA mediated inhibition of MDK: H441 cells were plated in a 12-well plate at a density of $1 \times 10^5$ per well and cultured overnight at 37° C. The following day 100 pmol of Smart Pool MK siRNA or nontargeting siRNA (Dharmacon, Perbio Science, France) was transfected using 2 μl Lipofectamine 2000 (Invitrogen Life Technologies, Carlsbad, Calif.) according to the manufacturer's instructions. Incubation time for transfection reagents was 24 hours, at which time medium was replaced with fresh regular medium. Cells were harvested 48 hours after transfection for immunoblotting and cell growth assays.

Cell viability assay: H441 cells, A549 cells, H520 cells, HEK293 cells and NHLF were plated in 24-well plates at a density of $1 \times 10^5$ cells and cultured at 37° C. for 24 hours. Medium was removed by aspiration and replaced with fresh culture medium containing iMDK dissolved in DMSO (10, 50, 100, 500 nmol/L). DMSO alone was used as the control. Cells were treated for 48 hours and collected by trypsinization. Viable cells were assessed by trypan blue exclusion. Recombinant MDK was purchased from R&D Systems (Minneapolis, Minn.) and reconstituted in water for block experiments. For MDK block experiments, H441 cells were cultured in Dulbecco's modified Eagle medium supplemented with 1% heat-inactivated fetal bovine overnight and recombinant MDK (25 nM) or/and iMDK (25 nM) was added for an additional 48 hours.

Hoechst staining: the morphologic characteristics of apoptosis were evaluated using Hoechst 33342 dye (Molecular Probes, Eugene, Oreg.), which stains DNA. Cells were incubated with 1 μg/ml Hoechst dye and then visualized under a fluorescence microscope (IX81, Olympus Medical Systems Corp., Tokyo, Japan) (Ogawa N, et al., Int. J. Cancer. 1997; 73:367-70).

Flow cytometric analysis for apoptosis: cells were plated in 24-well plates at a density of $0.5 \times 10^5$ cells per well 1 day before the treatments. After 72 hours, cells were harvested and washed once with PBS. Cells were resuspended in PBS containing 0.2% Triton X-100 and 1 mg/ml RNase for 5 min at room temperature and then stained with propidium iodide at 50 μg/ml to determine sub-G0/G1 DNA content using a FACScan. Doublets, cell debris, and fixation artifacts were gated out, and sub-G0/G1 DNA content was determined using Cell Quest Ver. 3.3 software.

Mouse experiments: human lung cancer xenografts were established in 6-wk-old female BALB/c nude mice (Charles River Laboratories Japan, Kanagawa, Japan) by subcutaneous (s.c.) inoculation of H441 cells ($1 \times 10^6$/50 μl) mixed with Matrigel® (BD Pharmingen, San Diego, Calif.; 50 μl) into the dorsal flank (Watanabe N, et al., Clin. Cancer Res. 2008; 14:4631-9). The mice were randomly assigned into three groups (n=8 per group) 14 days after tumor inoculations. One group of mice was intraperitonially injected with 100 μl solution containing iMDK (9 mg/kg) three days per week (on days 1, 3, 5, 8, 10) and another group of mice was injected five days per week (on days 1, 2, 3, 4, 5, 8, 9, 10). DMSO was injected into the control group. Tumors were measured two to three times a week, and tumor volume was calculated as $a \times b^2 \times 0.5$, where a and b were large and small diameters, respectively. On day 10, all mice were sacrificed after body weight was measured and tumors were removed and prepared for histology. For analysis of serum AST and ALT, blood was drawn from the heart 48 hours after intraperitonially injected with 100 μl solution containing iMDK (9 mg/kg). DMSO was injected into the control group and four mice were used for each group.

For immunohistochemistry, sections were sequentially deparaffinized through a series of xylene, graded ethanol, and water immersion steps. After being autoclaved in 0.2% citrate buffer for 15 minutes, sections were incubated with 3% hydrogen peroxide for 30 minutes to block endogenous peroxidase activity. A primary antibody specific for PI3 kinase p85, phosphorylated-PI3K p85 (Tyr458)/p55 (Tyr199) from Cell Signaling Technology and for MDK from Abcam were used. Specimens were incubated overnight at 4° C. with a 1:200 dilution of antibody followed by three washes with TBS. The slides were treated with streptoavidin-biotin complex (Envision System labeled polymer, horseradish peroxidase (HRP), Dako, Carpinteria, Calif.) for 60 minutes at a dilution of 1:100. Immunoreactions were visualized using a 3,3'-diaminobenzidine (DAB) substrate-chromogen solution (Dako Cytomation Liquid DAB Substrate Chromogen System, Dako) and counterstained with hematoxylin. Sections were immersed in an ethanol and xylene bath and mounted for examination.

Terminal deoxynucleotidyltransferase-mediated dUTP-biotin nick end labeling (TUNEL) staining was performed using the DeadEnd fluorometric TUNEL system (Promega, Madison, Wis.) according to the manufacturer's protocol.

Statistical analysis: Statistically significant differences between means and medians of the study groups were evaluated using Student's t-test. Statistical significance was defined as p<0.01.

Inhibition of MDK Reduces Viability of H441 Lung Adenocarcinoma Cells

Figure 2A:
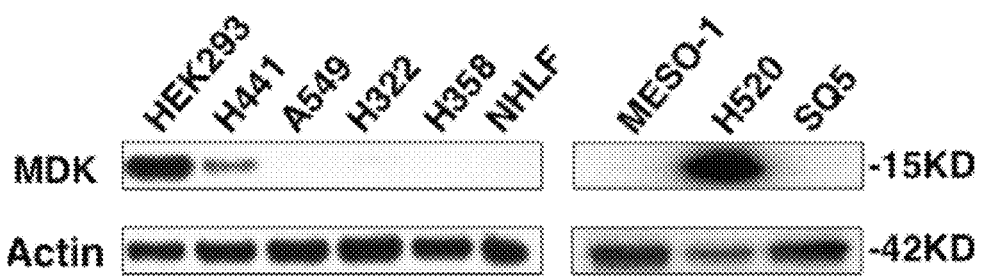
FIG. 2A-2C depict MDK knockdown inhibiting cell growth of H441 lung adenocarcinoma cells.
Figure 2B:
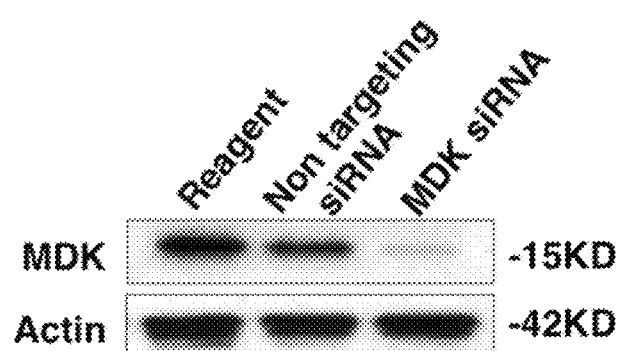
Figure 2C:
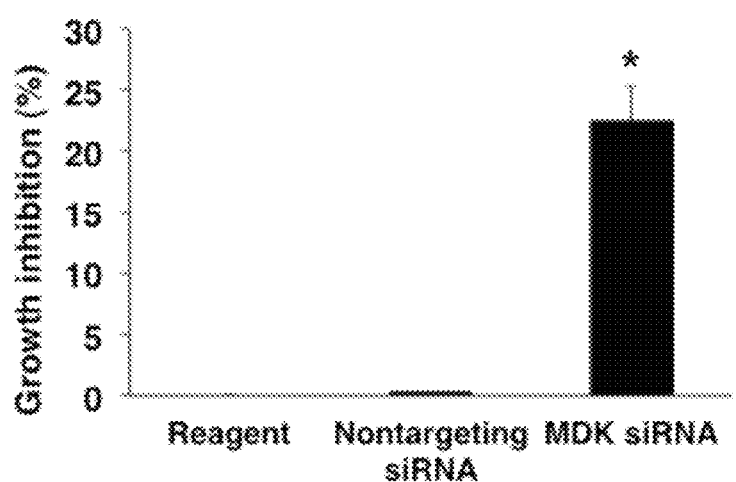

In order to find a NSCLC cell line that is dependent on MDK for cell growth, the endogenous expression of MDK protein in four different NSCLC cell lines and NHLF (Normal Human Lung Fibroblast) cells was assessed. HEK293 embryonic kidney cells were used as a positive control for MDK expression. As shown in FIG. 2A, MDK was detected in HEK293 cells, H441 lung adenocarcinoma cells and H520 human lung squamous cell carcinoma cells but not in A549, H322 and H358 lung adenocarcinoma cells, SQ5 lung squamous cell carcinoma cells and MESO-1 malignant mesothelioma cells. MDK was not expressed in non-transformed NHLF cells. The H441 cell line is derived from a NSCLC lung tumor that has a KRAS mutation. Activated RAS are the most common mutations associated with pulmonary adenocarcinomas in the Caucasian population and effective treatments for this disease have not yet been identified (Reidy K J, et al., Development. 2009; 136:3979-89). In order to determine whether H441 cells depend on MDK for cell viability, MDK was inhibited using siRNA and cell growth in the presence and absence of MDK was examined. As shown in FIG. 2B, 48 hours after transfection, MDK siRNA suppressed MDK in H441 cells compared to non-targeting siRNA. Inhibition of MDK significantly inhibited cell growth (P<0.01; FIG. 2C). These results demonstrate that targeting MDK is an effective strategy for suppressing cell growth of MDK-expressing non-small cell lung cancer.

iMDK Inhibits Endogenous MDK Expression in H441 Lung Adenocarcinoma Cells

Figure 3A:
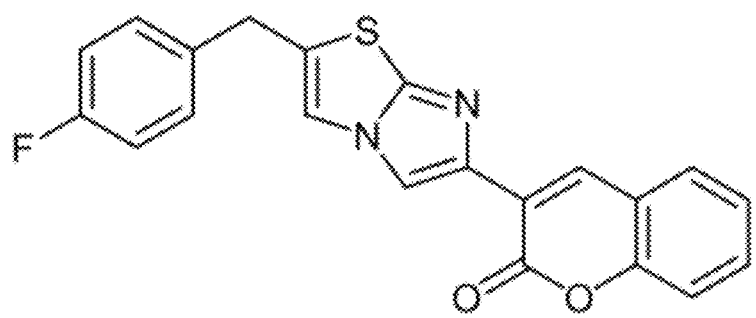
FIG. 3A-3B depict the small molecule compound iMDK inhibiting endogenous MDK expression in H441 lung adenocarcinoma cells.
Figure 3B:
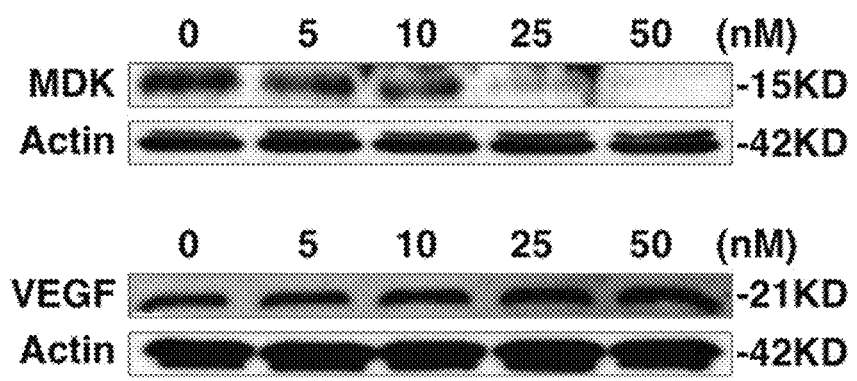
Figure 4A:
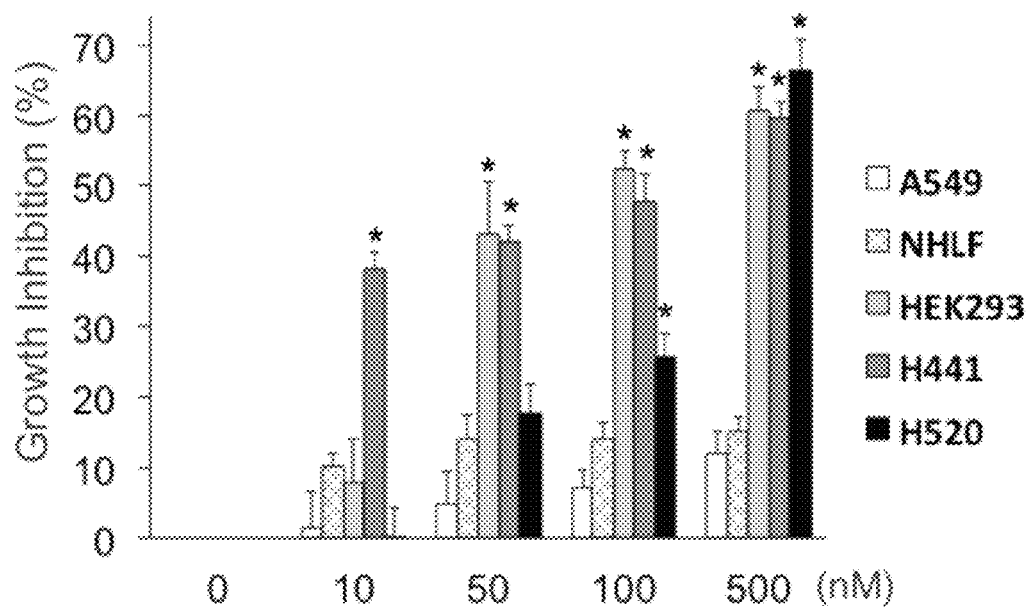
FIG. 4A-4B depict iMDK induced cell death in MDK expressing non-small cell lung carcinoma cells but not in MDK negative non-small cell lung carcinoma cells and normal cells.
Figure 4B:
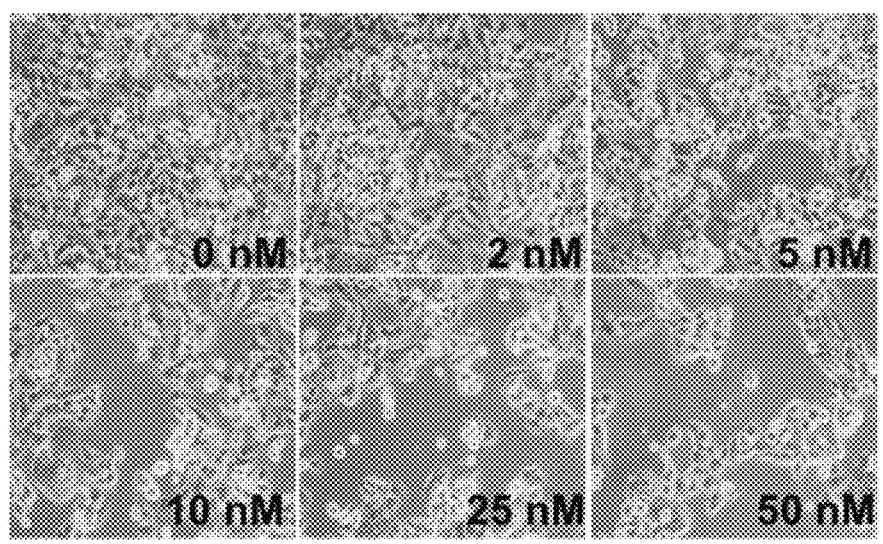

In order to find a therapeutic compound that inhibits MDK expression, a MDK reporter cell line by stably transfecting HEK293 cells with a MDK promoter-fused luciferase construct was developed. This modified cell line was used to screen 44,000 compounds at the Drug Discovery Center at the University of Cincinnati. See Example 1. Detection of luciferase activity was used to identify MDK inhibitors. In this screening, a compound (3-[2-(4-fluorobenzyl)imidazo[2,1-beta][1,3]thiazol-6-yl]-2H-chromen-2-one; FIG. 3A; iMDK; Example compound 2) that reproducibly inhibited endogenous MDK protein expression was identified. The effectiveness of iMDK for its ability to specifically inhibit the expression of MDK in H441 cells was assessed. As shown in FIG. 3B, iMDK inhibited endogenous MDK in a dose-dependent fashion but did not inhibit another growth factor VEGF in H441 lung adenocarcinoma cells 48 hours after treatment.

iMDK Inhibits Cell Viability of MDK-Expressing Non-Small Cell Lung Carcinoma Cells To further determine the effectiveness and specificity of iMDK in suppressing MDK-expressing tumor cells, both MDK-expressing and non MDK-expressing cells were treated with iMDK and cell viability using the trypan blue exclusion was assessed. MDK is expressed in HEK293 embryonic kidney cells, H441 lung adenocarcinoma cells and H520 lung squamous cell carcinoma cells but not in A549 lung carcinoma cells or non-transformed NHLF cells (FIG. 2A). These five cell lines were treated with a range of iMDK concentrations (0 to 500 nM) and cell number was assessed 48 hours after treatment. iMDK dose-dependently inhibited cell growth of MDK-expressing HEK293, H441 and H520 cells but not the non MDK-expressing A549 cells (FIG. 4A) or non-transformed NHLF cells (FIG. 4A). Morphologically, growth suppression of H441 cells was dose-dependently observed 48 hours after treatment with iMDK (FIG. 4B). The suppression of cell growth by iMDK was partially blocked by pretreatment of recombinant MDK (25 nM), suggesting the suppressive effect on cell growth by iMDK is mediated at least in part by the inhibition of MDK expression.

iMDK Induces Apoptosis in H441 Lung Adenocarcinoma Cells

Figure 5A:
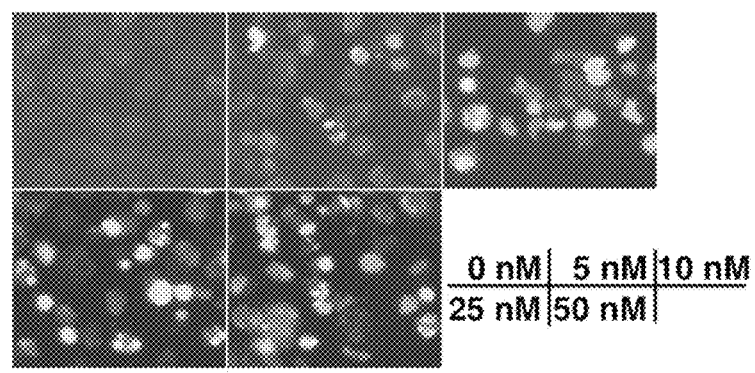
FIG. 5A-5C depict iMDK induction of apoptosis in H441 lung adenocarcinoma cells.
Figure 5B:
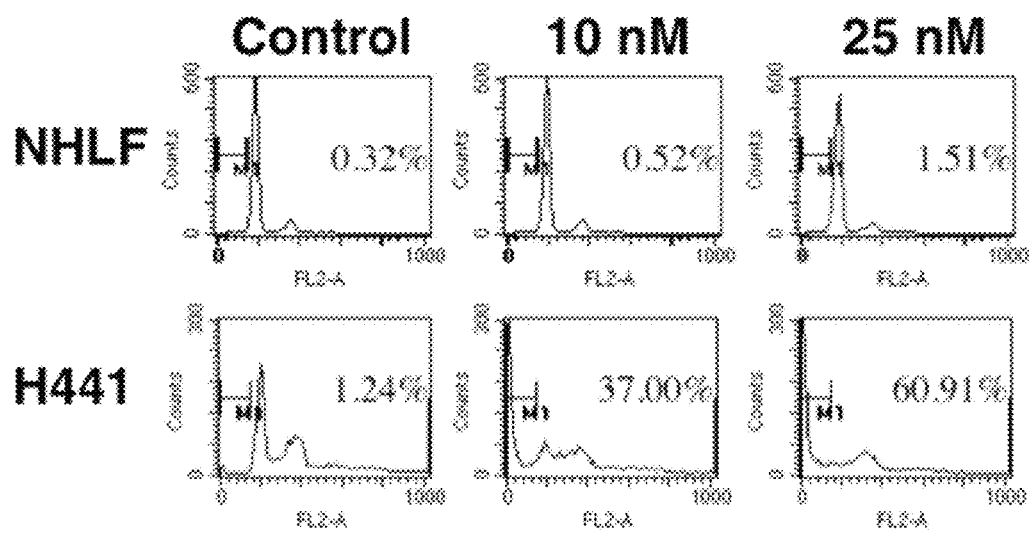
Figure 5C:
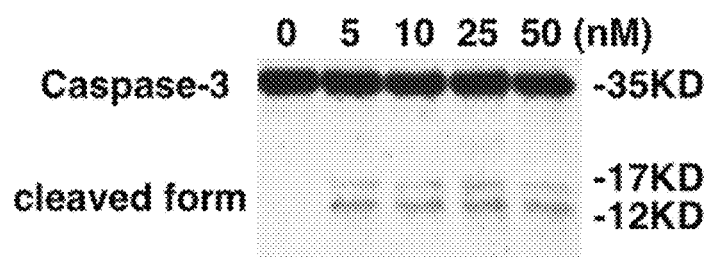
Figure 6A:
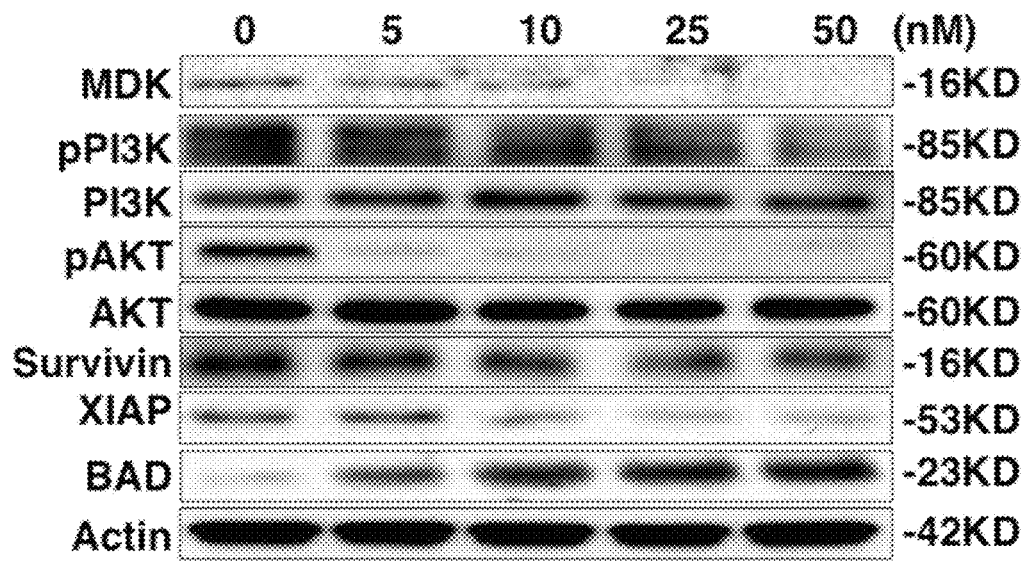
FIG. 6A-6B depict iMDK inhibition of the PI3K/AKT pathway and influence of the apoptosis pathway.
Figure 6B:
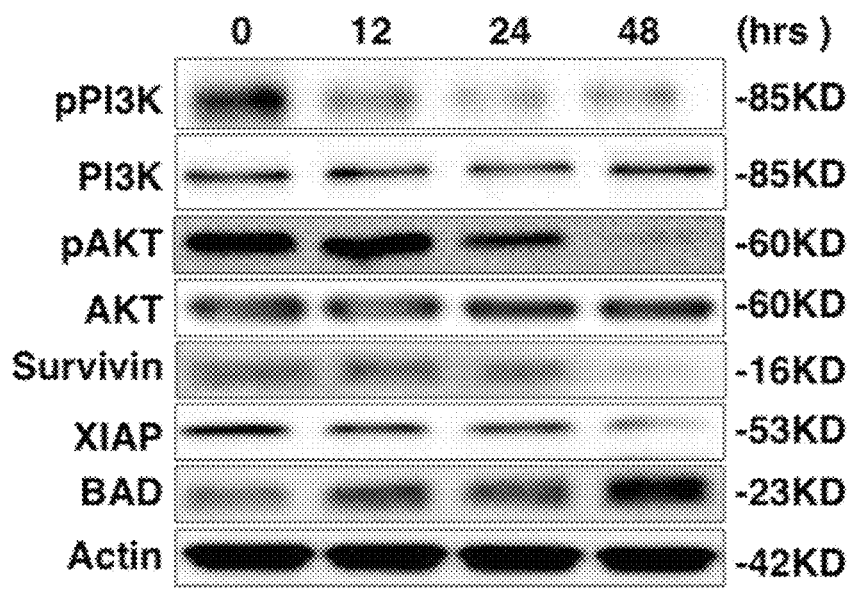
Figure 7A:
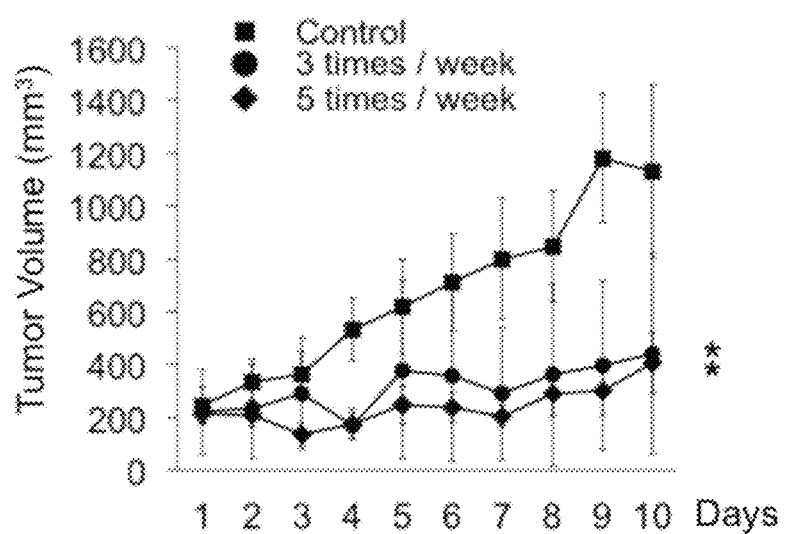
FIG. 7A-7B depict iMDK reduction of lung adenocarcinoma tumor growth in a xenograft mouse model.
Figure 7B:
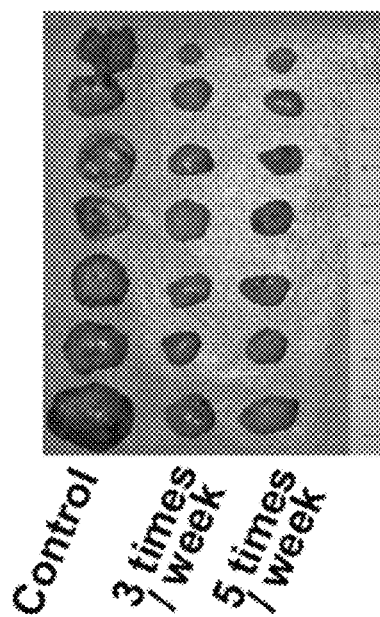
Figure 7C:
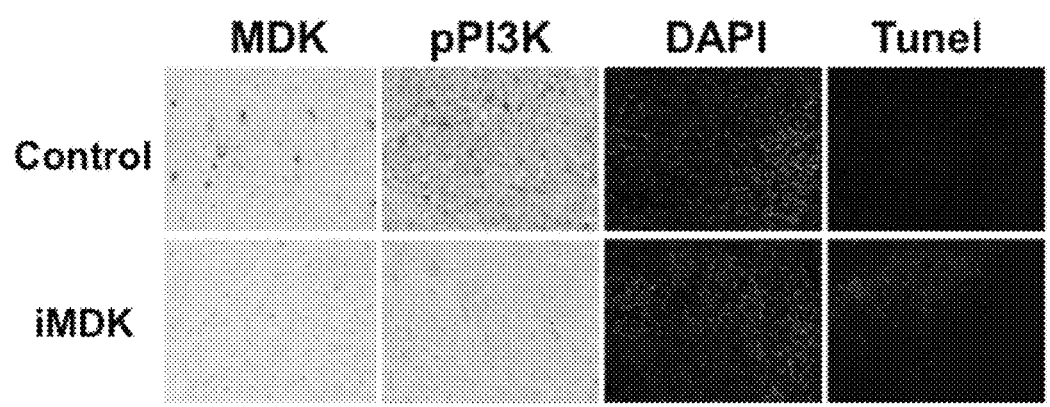
FIG. 7C depicts intraperitoneal administration of iMDK suppressed MDK expression and PI3 kinase phosphorylation, and induced apoptosis in H441 xenograft tumor in vivo. Tunel staining showed that apoptosis was induced in H441 xenograft tumors after iMDK treatment. Photomicrographs were taken at a magnification of 200×.

In order to understand the mechanism by which iMDK inhibits the growth of H441 cells, the cells for apoptosis 48 hours after treatment with iMDK was assessed. As shown in FIG. 5A, highly condensed and partly fragmented nuclei were observed in H441 cells treated with iMDK. iMDK induced nuclear fragmentation in a dose-dependent manner, likely indicating that iMDK induced apoptosis. sub-G0/G1 DNA content of H441 cells was highly increased from 1.24% (DMSO control) to 37.00% (10 nM) and 60.91% (25 nM) 72 hours after treatment with iMDK. However, sub-G0G1 DNA content of NHLF cells was minimally increased from 0.32% (DMSO control) to 0.52% (10 nM) and 1.51% (25 nM) after treatment with iMDK (FIG. 5B). These results again indicate that iMDK selectively induces apoptosis in MDK-expressing H441 lung adenocarcinoma cells but not in normal NHLF cells that do not express MDK. As shown in FIG. 5C, cleaved forms of caspase-3, a marker of apoptosis, was induced by iMDK even at the lowest concentrations (5 nM) in H441 cells 48 hours after treatment. Collectively, these results show that iMDK induces apoptosis of MDK-expressing H441 lung adenocarcinoma cells but not non-tumor NHLF cells that lack MDK.

iMDK Suppresses the PI3K and Induces the Apoptotic Pathways in H441 Lung Adenocarcinoma Cells PI3K is involved in tumorigenesis by activating AKT, which in turn increases anti-apoptotic factors, such as XIAP and survivin, and decreases a pro-apoptotic factor BAD (Jazirehi A R, et al., American Journal of Cancer Res. 2012; 2:178-91; Kaneko R, et al., J. Biol. Chem. 2007; 282:19273-81; Uddin S, et al., Clin. Cancer Res. 2005; 11:3102-8). Since MDK activates PI3K activity, whether the PI3K pathway was suppressed by iMDK-mediated MDK inhibition was examined (Sumida A, et al., Cardiovascular Research. 2010; 86:113-21). Phosphorylation of PI3K and AKT were suppressed by iMDK in a dose- and time-dependent manner (FIGS. 6A and 6B), indicating that the PI3K/AKT pathway is inhibited by iMDK. Anti-apoptotic factors, XIAP and survivin, were reduced while the pro-apoptotic factor, BAD, was induced by iMDK in a dose- and time-dependent fashion (FIGS. 6A and 6B), indicating that the apoptotic pathway is induced by iMDK. These results indicate that iMDK suppresses the PI3K/AKT pathway and in turn causes apoptosis in H441 lung adenocarcinoma cells.

iMDK Suppresses Lung Tumor Growth and Induces Apoptosis in a Xenograft Mouse Model In order to determine whether systemic administration of iMDK suppresses tumor growth in vivo, iMDK (9 mg/kg) was intraperitoneally injected either 3 or 5 times a week into nude mice bearing xenografts derived from H441 lung adenocarcinoma cells 14 days after tumor inoculation. Lung tumor xenografts continued to grow in the control (DMSO treated) group while lung tumor growth was arrested in iMDK-treated groups. The volume of the tumors in the iMDK-treated group was significantly lower than that in the control group (FIGS. 7A and 7B). MDK and phosphorylated PI3K were observed in lung tumors of the control mice but not in the iMDK-treated mice (FIG. 7C). Tunel staining detected DNA fragmentation, an indicator of apoptosis, in tumors of iMDK-treated mice but not in those from control mice (FIG. 7C). iMDK did not influence body weight and serum levels of AST and ALT, suggesting no systemic toxicity. These results indicate that iMDK is a therapeutic drug targeting MDK-expressing lung cancer without side effects.

The success of small molecules specifically inhibiting EGFR function in mutant EGFR-driven lung adenocarcinoma has promoted molecular targeted therapy for lung cancer (Kobayashi S, et al., N. Engl. J. Med. 2005; 352: 786-92; Kwak E L, et al., N. Engl. J. Med. 2010; 363:1693-703). Targeted treatments for mutant KRAS-driven lung adenocarcinoma and lung squamous cell carcinoma have not been developed other than chemotherapy that target both cancer cells and normal proliferating cells. A small molecule compound iMDK has been identified that inhibits the expression of MDK, a tumor-promoting growth factor. iMDK inhibited the PI3K/AKT pathway and suppressed KRAS-mutated lung adenocarcinoma by inducing apoptosis in vitro and in vivo. iMDK did not impair the viability of normal proliferating NHLF cells. Further, no obvious systemic toxicity was observed in iMDK-treated mice, supporting the potential utility of iMDK for therapy of MDK-dependent lung adenocarcinoma.

Since MDK is highly expressed in hepatocellular, gastric, colorectal and prostate cancers, the MDK inhibitor iMDK may be useful for treating non-pulmonary tumors as well. Also, MDK expression is associated with various inflammatory diseases, including rheumatoid arthritis and atherosclerosis (Maruyama K, et al., Arthritis Rheum. 2004; 50:1420-9). Mdk-knockout mice are resistant to the development of rheumatoid arthritis by preventing inflammatory leukocyte migration and osteoclast differentiation. The knockout mice are also resistant to neointimal formation, a common feature of atherosclerosis and restenosis (Horiba M, et al., J. Clin. Invest. 2000; 105:489-95). These results suggest that iMDK may be useful for treating these non-tumorigenic diseases as well.

In addition to iMDK, a small molecule compound (Example compound No. 1) that also suppressed the expression of MDK was identified which exerted a similar dose effect to iMDK. Although iMDK suppressed endogenous MDK protein expression, the mechanism by which iMDK inhibited MDK is not understood. Since the extent of inhibition of MDK RNA was less than that of MDK protein (data not shown), iMDK may target the MDK protein directly. Biotin-tagged iMDK or radioisotope-labeled iMDK will be required to identify potential sites of action of MDK and the mechanism(s) by which iMDK inhibits the expression of MDK. The MDK inhibitor, iMDK, suppressed non-small cell lung cancer expressing MDK in vitro and in vivo without harming normal cells.

Example 3—Inhibition of Midkine Expression

Figure 8A:
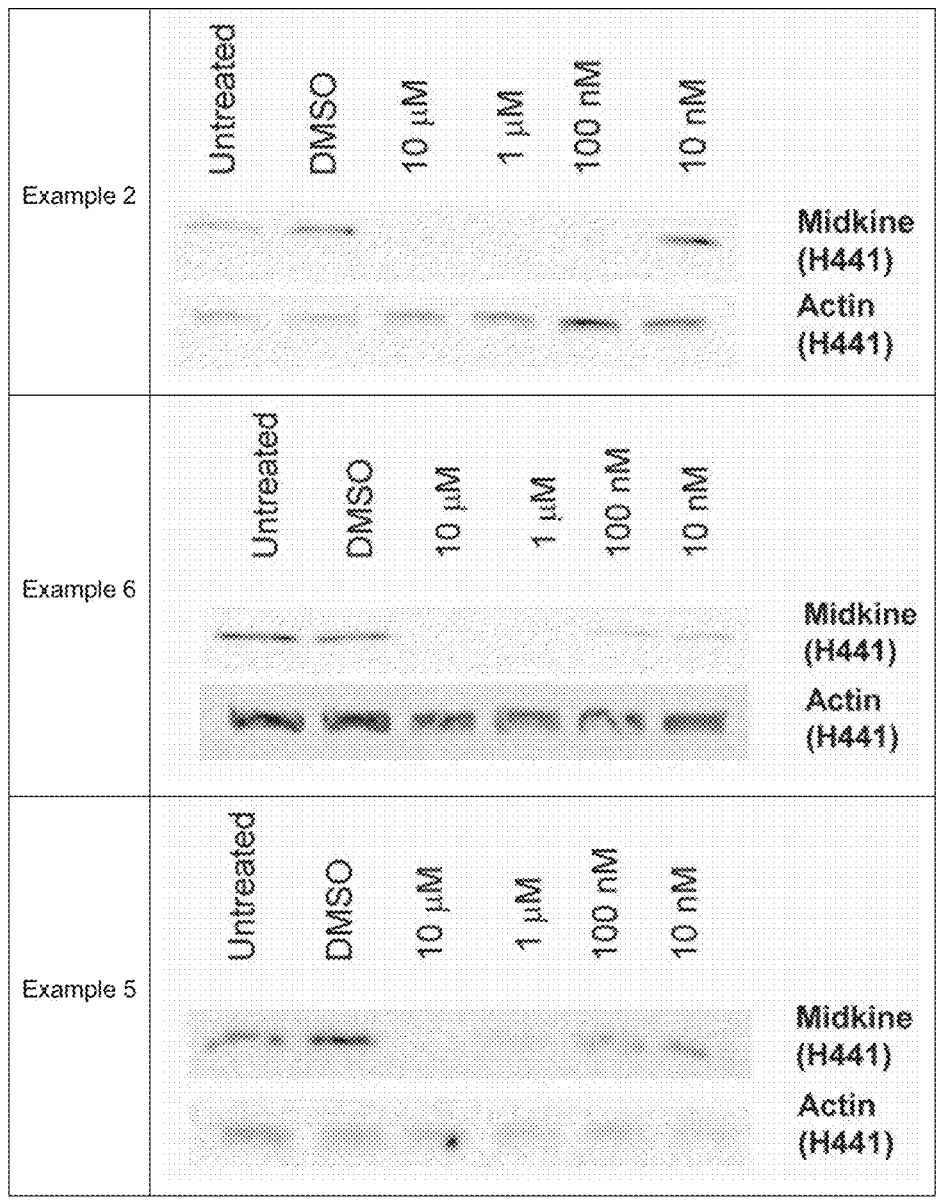

Midkine protein expression in response to various concentrations of a compound from TABLE 2 in H441 was measured using Western blots. Briefly, H441 cells were treated with the compounds at the indicated final concentrations. 24 hours after treatment, cells were lysed and cell extracts were used for western blotting as described previously (Maeda Y, et al., J Biol Chem.; 281:9600-6). The western blot membranes were then incubated with anti-Midkine (cat# ab52637, abcam) and anti-Actin (cat# A2066, Sigma-Aldrich) and probed with horseradish peroxidase-coupled secondary antibodies. Western blots were developed by Western HRP Substrates (Millipore) according to the manufacturers' instructions. Western blots are shown in FIG. 8A and FIG. 8B. All compounds of TABLE 2 inhibited midkine expression.

TABLE 2

| Example | Compound structure | Concentration to inhibit midkine protein expression |
| --- | --- | --- |
| 1 | 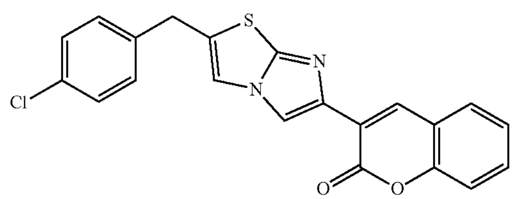 [SMILES: O=c1oc2ccccc2cc1-c1cn2cc(Cc3ccc(Cl)cc3)sc2n1] | |
| 2 | 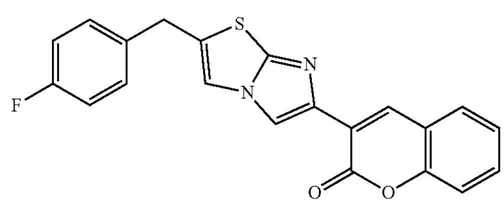 [SMILES: O=c1oc2ccccc2cc1-c1cn2cc(Cc3ccc(F)cc3)sc2n1] | 100 nM |
| 5 | 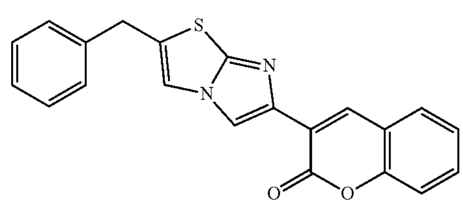 [SMILES: O=c1oc2ccccc2cc1-c1cn2cc(Cc3ccccc3)sc2n1] | 10 µM |
| 6 | 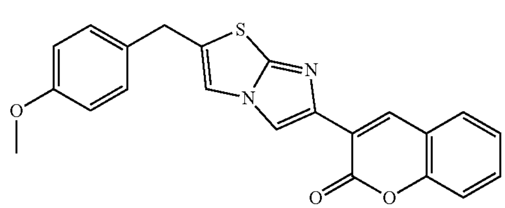 [SMILES: COc1ccc(Cc2cn3cc(-c4cc5ccccc5oc4=O)nc3s2)cc1] | 1 µM |

TABLE 2-continued

| Example | Compound structure | Concentration to inhibit midkine protein expression |
|---|---|---|
| 7 | 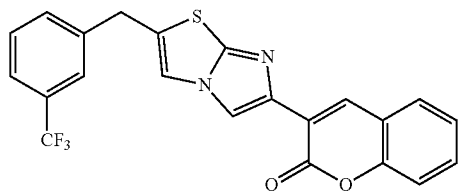 [SMILES: O=c1oc2ccccc2cc1-c1cn2cc(Cc3cccc(C(F)(F)F)c3)sc2n1] | 100 nM |
| 8 | 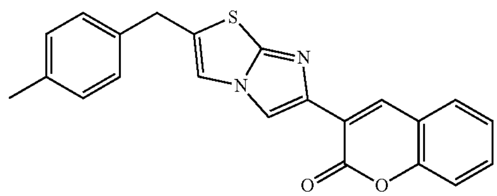 [SMILES: Cc1ccc(Cc2cn3cc(-c4cc5ccccc5oc4=O)nc3s2)cc1] | 1 μM |
| 9 | 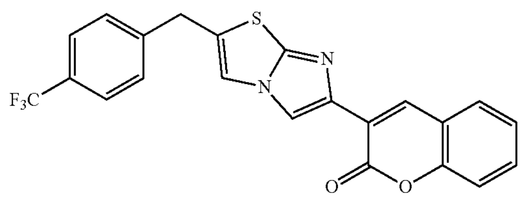 [SMILES: O=c1oc2ccccc2cc1-c1cn2cc(Cc3ccc(C(F)(F)F)cc3)sc2n1] | 1 μM |
| 10 | 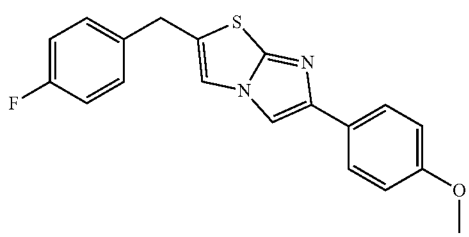 [SMILES: COc1ccc(-c2cn3cc(Cc4ccc(F)cc4)sc3n2)cc1] | 10 μM |

Example 4—Cytotoxicity of Compounds

Cell toxicity was assessed by cell detachment observed under a microscope 24 hours after treatment with Compounds 1, 2, 5, 6, 7, 8, 9, and 10 at a final concentration of 10 μM.

All tested compounds were toxic.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of treating a subject having a disorder selected from the group consisting of an MDK-expressing-lung cancer, and an MDK-expressing-renal cancer, comprising: administering to a subject in need thereof an effective amount of a compound of formula (I):

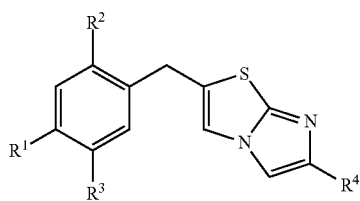
(I)

or a pharmaceutically acceptable salt thereof,
wherein:
$R^1$ is hydrogen, —OCH$_3$, —CH$_3$, —CF$_3$ or halogen;
$R^2$ is hydrogen or chlorine;
$R^3$ is hydrogen, chlorine or —CF$_3$; and
$R^4$ is

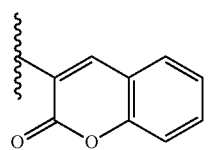 or - 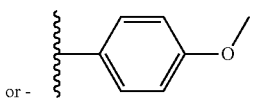.

2. The method of claim 1, wherein:
$R^1$ is hydrogen or halogen;
$R^2$ is hydrogen or chlorine;
$R^3$ is hydrogen or chlorine, when $R^1$ is hydrogen then $R^2$ and $R^3$ are chlorine, and when $R^2$ and $R^3$ are chlorine then $R^1$ is hydrogen.

3. The method of claim 1, wherein $R^1$ is selected from hydrogen, —OCH$_3$ and halogen; and $R^2$ and $R^3$ are hydrogen.

4. The method of claim 3, wherein $R^1$ is fluorine.

5. The method of claim 1, wherein the compound of formula (I) has the structure of formula (II):

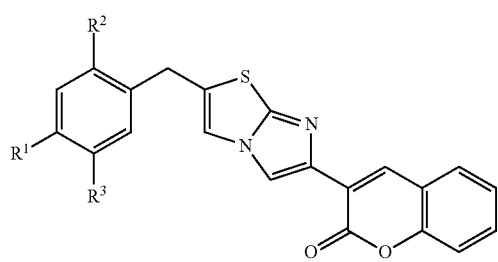
(II)

or a pharmaceutically acceptable salt thereof,
wherein:
$R^1$ is hydrogen, —OCH$_3$, or halogen;
$R^2$ is hydrogen or chlorine;
$R^3$ is hydrogen or chlorine.

6. The method of claim 1, wherein formula (I) is selected from the group consisting of:

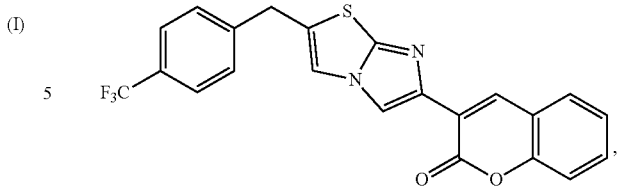

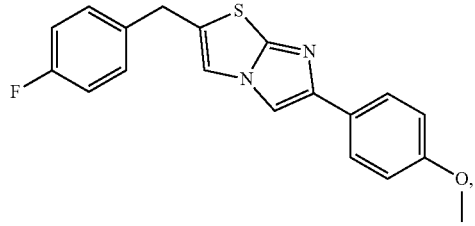

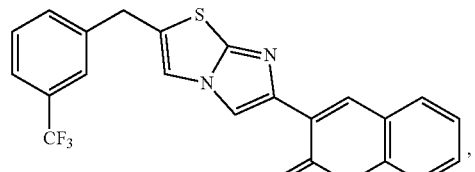

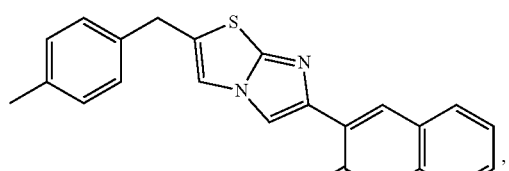

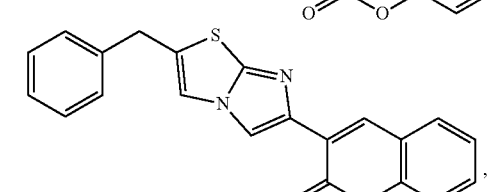

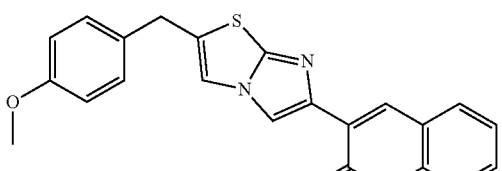

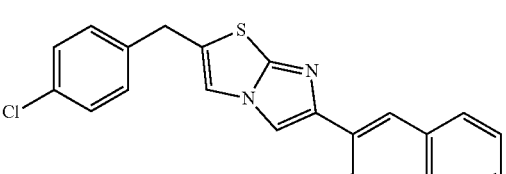

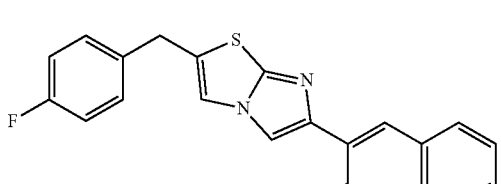

-continued
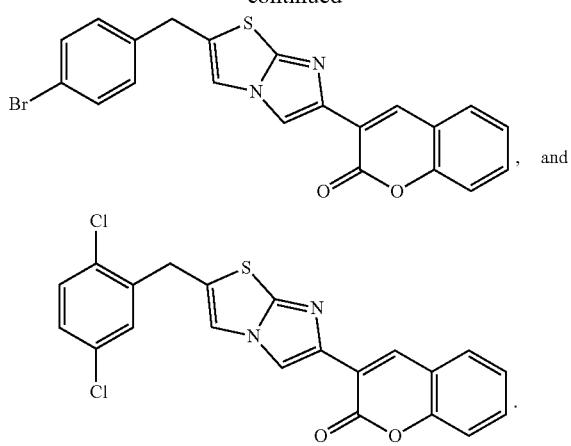
, and
7. The method of claim 1, wherein formula (I) is:
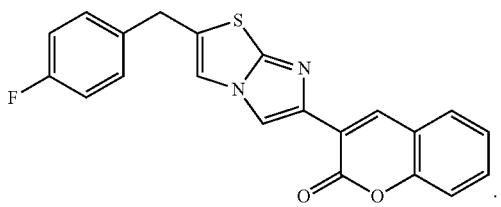 [SMILES: O=c1oc2ccccc2cc1-c1cn2cc(Cc3ccc(F)cc3)sc2n1]
.
8. The method of claim 1, wherein the MDK-expressing-lung cancer is selected from the group consisting of an MDK-expressing-squamous cell carcinoma, and an MDK-expressing-adenocarcinoma.
9. The method of claim 1, wherein the subject is mammalian.
* * * * *